United States Patent
Firth et al.

(12)

(10) Patent No.: US 6,573,053 B1
(45) Date of Patent: Jun. 3, 2003

(54) ANALYSIS METHOD

(75) Inventors: Greg Firth, Hitchin (GB); Rajesh Muru Odedra, Stevenage (GB)

(73) Assignee: Amersham Biosciences UK Limited (GB)

( * ) Notice: Subject to any disclaimer, the term of this patent is extended or adjusted under 35 U.S.C. 154(b) by 0 days.

(21) Appl. No.: 09/890,848

(22) PCT Filed: Feb. 4, 2000

(86) PCT No.: PCT/GB00/00346

§ 371 (c)(1),
(2), (4) Date: Sep. 24, 2001

(87) PCT Pub. No.: WO00/46402

PCT Pub. Date: Aug. 10, 2000

(30) Foreign Application Priority Data

Feb. 5, 1999 (EP) .............................................. 99300873

(51) Int. Cl.⁷ ................................................. C12Q 1/68
(52) U.S. Cl. .......................... 435/6; 536/23.1; 536/24.3
(58) Field of Search .............................. 435/6; 536/23.1, 536/24.3; 935/76, 77, 78

(56) References Cited

U.S. PATENT DOCUMENTS

| | | | |
|---|---|---|---|
| 5,376,526 A | * | 12/1994 | Brown et al. |
| 5,494,810 A | * | 2/1996 | Barany et al. |
| 5,710,000 A | | 1/1998 | Sapolsky et al. |
| 6,300,071 B1 | * | 10/2001 | Vuylsteke et al. |
| 6,372,434 B1 | * | 4/2002 | Weissman et al. |

FOREIGN PATENT DOCUMENTS

| | | |
|---|---|---|
| WO | WO 93/22462 A | 11/1993 |
| WO | WO 94/08052 A | 4/1994 |
| WO | WO 95/12688 A | 5/1995 |
| WO | WO 96/41002 A | 12/1996 |
| WO | WO0053802 * | 9/2000 |

OTHER PUBLICATIONS

Agrawal et al., PNAS, USA 86: 7790–7794 (1989).*
Smith, J., et al. "Mutation Detection with MUTH, MUTL, and MUTS Mismatch Repair Proteins" Proceedings of the National Academy of Sciences of USA vol. 93, Apr. 1, 1996, pp. 4374–4379.

* cited by examiner

*Primary Examiner*—Ethan Whisenant
(74) *Attorney, Agent, or Firm*—Royal N. Ronning, Jr.; Stephen G. Ryan

(57) ABSTRACT

A method of comparing genomic DNA from two individuals who share a phenotype, cutting the DNA into fragments long enough to contain on average one or several polymorphisms; combining the fragments under hybridisation conditions and recovering mismatch—free heterohybrids, wherein adapters resistant to nuclease digestion are ligated to the ends of the genomic fragments. A related method uses pooled genomic DNA from individuals with a common phenotype. Another related method uses restricted nucleic acid fragments likely to contain on average less than one natural polymorphism.

11 Claims, 8 Drawing Sheets

SEQUENCE LISTING

```
<160> NUMBER OF SEQ ID NOS: 18

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Contains
      Phosphorothioate linkages

<400> SEQUENCE: 1
cattcggatg ttgatcgcgg ccgcttgtct gca                                33

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Contains
      Phosphorothioate linkages

<400> SEQUENCE: 2
gacaagcggc cgcgatcaag taggcttac                                    29

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Contains
```

-continued

```
      Phosphorothioate linkages

<400> SEQUENCE: 3
gtaagcctac ttgatcgcgg ccgcttgtct gca                              33

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Contains
      Phosphorothioate linkages

<400> SEQUENCE: 4
gacaagcggc cgcgatcaac atccgaatg                                   29

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
gtttcttctg caggtcgact ctagagga                                    28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
gtttcttcta tagggaattc gagctcgg                                    28

<210> SEQ ID NO 7
<211> LENGTH: 132
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
cacttgggac tttggattgg tcactactga cattttgtat gcagcagcca cctgttctgg    60
tgtgtgtgtg tgtgtgtgtg tgtgtgtgtg tgtcttgttt gttttaatgc aagcaagaat   120
ggaaacaaag ac                                                      132

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
aaagcctaca actagccgtc cgcttgtct                                   29

<210> SEQ ID NO 9
<211> LENGTH: 28
<212> TYPE: DNA
```

```
<213> ORGANISM: Artificial Sequence
<220> FEATURE:
<223> OTHER INFORMATION: Description of Artificial Sequence: synthetic
      oligonucleotide containing methyl phosphonate

<400> SEQUENCE: 9
gacaagcgga cgcgatcaac atccgaaa                                          28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide containing methyl phosphonate

<400> SEQUENCE: 10
gacaagcgga cggctagttg taggcttt                                          28

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: synthetic
      oligonucleotide containing methyl phosphonate

<400> SEQUENCE: 11
ccttcggccg atgaccgtcg ttgtctgca                                         29

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide containing methyl phosphonate

<400> SEQUENCE: 12
gacaacgacg gtgtagccgg cttcc                                             25

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: synthetic
      oligonucleotide containing methyl phosphonate

<400> SEQUENCE: 13
ggaagccggc tacaccgttg ttgtctgca                                         29

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide containing methyl phosphonate

<400> SEQUENCE: 14
gacaacgacg gtcatcggcc gaagg                                             25

<210> SEQ ID NO 15
<211> LENGTH: 1750
<212> TYPE: DNA
<213> ORGANISM: Artificial Sequence
```

<220> FEATURE:
<223> OTHER INFORMATION: Description of Artificial Sequence: lambda
      fragment

<400> SEQUENCE: 15

| | | | | | |
|---|---|---|---|---|---|
| ctgccctggc | tgagtgaggc | cgaccggcgg | ctgcaggtgc | agagtgattt | gccgtggtgg | 60 |
| ctggtctgcc | gggggacgat | tcataagttc | cgctgtgtgc | cgcatctcac | cgggcggcgc | 120 |
| tttgagcacg | gtgtgacgga | ctgttacaca | ctgttccggg | atgcttatca | tctggcgggg | 180 |
| attgagatgc | cggactttca | tcgtgaggat | gactggtggg | gtaacggcca | gaatctctat | 240 |
| ctggataatc | tggaggcgac | ggggctgtat | caggtgccgt | tgtcagcggc | acagccgggc | 300 |
| gatgtgctgc | tgtgctgttt | tggttcatca | gtgccgaatc | acgccgcaat | ttactgcggc | 360 |
| gacggcgagc | tgctgcacca | tattcctgaa | caactgagca | acgagagag | gtacaccgac | 420 |
| aaatggcagc | gacgcacaca | ctccctctgg | cgtcaccggg | catggcgcgc | atctgccttt | 480 |
| acggggattt | acaacgattt | ggtcgccgca | tcgaccttcg | tgtgaaaacg | ggggctgaag | 540 |
| ccatccgggc | actggccaca | cagctcccgg | cgtttcgtca | gaaactgagc | gacggctggt | 600 |
| atcaggtacg | gattgccggg | cgggacgtca | gcacgtccgg | gttaacggcg | cagttacatg | 660 |
| agactctgcc | tgatggcgct | gtaattcata | ttgttcccag | agtcgccggg | gccaagtcag | 720 |
| gtggcgtatt | ccagattgtc | ctgggggctg | ccgccattcg | cggatcattc | tttaccgccg | 780 |
| gagccaccct | tgcagcatgg | ggggcagcca | ttggggccgg | tggtatgacc | ggcatcctgt | 840 |
| tttctctcgg | tgccagtatg | gtgctcggtg | gtgtggcgca | gatgctggca | ccgaaagcca | 900 |
| gaactccccg | tatacagaca | acggataacg | gtaagcagaa | cacctatttc | tcctcactgg | 960 |
| ataacatggt | tgcccagggc | aatgttctgc | ctgttctgta | cggggaaatg | cgcgtggggt | 1020 |
| cacgcgtggt | ttctcaggag | atcagcacgg | cagacgaagg | ggacggtggt | caggttgtgg | 1080 |
| tgattggtcg | ctgatgcaaa | atgttttatg | tgaaaccgcc | tgcgggcggt | tttgtcattt | 1140 |
| atggagcgtg | aggaatgggt | aaaggaagca | gtaagggca | taccccgcgc | gaagcgaagg | 1200 |
| acaacctgaa | gtccacgcag | ttgctgagtg | tgatcgatgc | catcagcgaa | gggccgattg | 1260 |
| aaggtccggt | ggatggctta | aaaagcgtgc | tgctgaacag | tacgccggtg | ctggacactg | 1320 |
| agggaatac | caacatatcc | ggtgtcacgg | tggtgttccg | ggctggtgag | caggagcaga | 1380 |
| ctccgccgga | gggatttgaa | tcctccggct | ccgagacggt | gctgggtacg | gaagtgaaat | 1440 |
| atgacacgcc | gatcacccgc | accattacgt | ctgcaaacat | cgaccgtctg | cgctttacct | 1500 |
| tcggtgtaca | ggcactggtg | gaaaccacct | caaagggtga | caggaatccg | tcggaagtcc | 1560 |
| gcctgctggt | tcagatacaa | cgtaacggtg | gctgggtgac | ggaaaaagac | atcaccatta | 1620 |
| agggcaaaac | cacctcgcag | tatctggcct | cggtggtgat | gggtaacctg | ccgccgcgcc | 1680 |
| cgtttaatat | cgggatgcgc | aggatgacgc | cggacagcac | cacagaccag | ctgcagaaca | 1740 |
| aaacgctctg | | | | | 1750 |

<210> SEQ ID NO 16
<211> LENGTH: 5277
<212> TYPE: DNA
<213> ORGANISM: Artificial Sequence
<220> FEATURE:
<223> OTHER INFORMATION: Description of Artificial Sequence: synthetic
      plasmid

<400> SEQUENCE: 16

| | | | | | |
|---|---|---|---|---|---|
| tcgcgcgttt | cggtgatgac | ggtgaaaacc | tctgacacat | gcagctcccg | gagacggtca | 60 |

-continued

| | | | | |
|---|---|---|---|---|
| cagcttgtct | gtaagcggat | gccgggagca | gacaagcccg | tcaggcgcg tcagcgggtg | 120 |
| ttggcgggtg | tcgggctgg | cttaactatg | cggcatcaga | gcagattgta ctgagagtgc | 180 |
| accataaacg | acattactat | atatataata | taggaagcat | ttaatagaca gcatcgtaat | 240 |
| atatgtgtac | tttgcagtta | tgacgccaga | tggcagtagt | ggaagatatt ctttattgaa | 300 |
| aaatagcttg | tcaccttacg | tacaatcttg | atccggagct | tttctttttt tgccgattaa | 360 |
| gaattaattc | ggtcgaaaaa | agaaaggag | agggccaaga | gggagggcat tggtgactat | 420 |
| tgagcacgtg | actatacgtg | attaagcaca | caaaggcagc | ttggagtatg tctgttatta | 480 |
| atttcacagg | tagttctggt | ccattggtga | aagtttgcgg | cttgcagagc acagaggccg | 540 |
| cagaatgtgc | tctagattcc | gatgctgact | tgctgggtat | tatatgtgtg cccaatagaa | 600 |
| agagaacaat | tgacccggtt | attgcaagga | aaatttcaag | tcttgtaaaa gcatataaaa | 660 |
| atagttcagg | cactccgaaa | tacttggttg | gcgtgtttcg | taatcaacct aaggaggatg | 720 |
| ttttggctct | ggtcaatgat | tacggcattg | atatcgtcca | actgcatgga gatgagtcgt | 780 |
| ggcaagaata | ccaagagttc | ctcggtttgc | cagttattaa | aagactcgta tttccaaaag | 840 |
| actgcaacat | actactcagt | gcagcttcac | agaaacctca | ttcgtttatt cccttgtttg | 900 |
| attcagaagc | aggtgggaca | ggtgaacttt | tggattggaa | ctcgatttct gactgggttg | 960 |
| gaaggcaaga | gagccccgaa | agcttacatt | ttatgttagc | tggtggactg acgccagaaa | 1020 |
| atgttggtga | tgcgcttaga | ttaaatggcg | ttattggtgt | tgatgtaagc ggaggtgtgg | 1080 |
| agacaaatgg | tgtaaaagac | tctaacaaaa | tagcaaattt | cgtcaaaaat gctaagaaat | 1140 |
| aggttattac | tgagtagtat | ttatttaagt | attgtttgtg | cacttgcctg cggtgtgaaa | 1200 |
| taccgcacag | atgcgtaagg | agaaaatacc | gcatcaggaa | attgtaaacg ttaatatttt | 1260 |
| gttaaaattc | gcgttaaatt | tttgttaaat | cagctcattt | tttaaccaat aggccgaaat | 1320 |
| cggcaaaatc | cctataaat | caaagaata | gaccgagata | gggttgagtg ttgttccagt | 1380 |
| ttggaacaag | agtccactat | taagaacgt | ggactccaac | gtcaaagggc gaaaaaccgt | 1440 |
| ctatcagggc | gatggcccac | tacgtgaacc | atcaccctaa | tcaagttttt tggggtcgag | 1500 |
| gtgccgtaaa | gcactaaatc | ggaaccctaa | agggagcccc | cgatttagag cttgacgggg | 1560 |
| aaagccggcg | aacgtggcga | gaaaggaagg | gaagaaagcg | aaaggagcgg gcgctagggc | 1620 |
| gctggcaagt | gtagcggtca | cgctgcgcgt | aaccaccaca | cccgccgcgc ttaatgcgcc | 1680 |
| gctacagggc | gcgtcgcgcc | attcgccatt | caggctgcgc | aactgttggg aagggcgatc | 1740 |
| ggtgcgggcc | tcttcgctat | tacgccagct | ggcgaagggg | ggatgtgctg caaggcgatt | 1800 |
| aagttgggta | acgccagggt | tttcccagtc | acgacgttgt | aaaacgacgg ccagtgaatt | 1860 |
| gtaatacgac | tcactatagg | gcgaattgga | gctcgagcaa | taaagattct acaatactag | 1920 |
| cttttatggt | tatgaagagg | aaaaattggc | agtaacctgg | ccccacaaac cttcaaatga | 1980 |
| acgaatcaaa | ttaacaacca | taggatgata | atgcgattag | ttttttagcc ttatttctgg | 2040 |
| ggtaattaat | cagcgaagcg | atgatttttg | atctattaac | agatatataa atgcaaaaac | 2100 |
| tgcataacca | ctttaactaa | tactttcaac | attttcggtt | tgtattactt cttattcaaa | 2160 |
| tgtaataaaa | gtatcaacat | ctagaattcc | atggaatcga | tgcggccgca attcatcgat | 2220 |
| tagactagtc | tagatatcat | gtaattagtt | atgtcacgct | tacattcacg ccctcccccc | 2280 |
| acatccgctc | taaccgaaaa | ggaaggagtt | agacaacctg | aagtctaggt ccctatttat | 2340 |
| tttttatag | ttatgttagt | attaagaacg | ttatttatat | ttcaaatttt tcttttttt | 2400 |
| ctgtacagac | gcgtgtacgc | atgtaacatt | atactgaaaa | ccttgcttga gaaggttttg | 2460 |

```
ggacgctcga aggctttaat ttgcggtacc cagcttttgt tcccttagt gagggttaat    2520 tccgagcttg gcgtaatcat ggtcatagct gttcctgtg tgaaattgtt atccgctcac    2580
aattccacac aacataggag ccggaagcat aaagtgtaaa gcctggggtg cctaatgagt    2640
gaggtaactc acattaattg cgttgcgctc actgcccgct ttccagtcgg gaaacctgtc    2700
gtgccagctg cattaatgaa tcggccaacg cgcggggaga ggcggtttgc gtattgggcg    2760
ctcttccgct tcctcgctca ctgactcgct gcgctcggtc gttcggctgc ggcgagcggt    2820
atcagctcac tcaaaggcgg taatacggtt atccacagaa tcaggggata acgcaggaaa    2880
gaacatgtga gcaaaaggcc agcaaaaggc caggaaccgt aaaaaggccg cgttgctggc    2940 gttttccat aggctcggcc ccctgacga gcatcacaaa aatcgacgct caagtcagag    3000
gtggcgaaac ccgacaggac tataaagata ccaggcgttc ccccctggaa gctccctcgt    3060
gcgctctcct gttccgaccc tgccgcttac cggatacctg tccgcctttc tcccttcggg    3120
aagcgtggcg ctttctcaat gctcacgctg taggtatctc agttcggtgt aggtcgttcg    3180
ctccaagctg ggctgtgtgc acgaaccccc cgttcagccc gaccgctgcg ccttatccgg    3240
taactatcgt cttgagtcca acccggtaag acacgactta tcgccactgg cagcagccac    3300
tggtaacagg attagcagag cgaggtatgt aggcggtgct acagagttct tgaagtggtg    3360
gcctaactac ggctacacta aggacagt atttggtatc tgcgctctgc tgaagccagt    3420
taccttcgga aaaagagttg gtagctcttg atccggcaaa caaccaccg ctggtagcgg    3480 tggtttttt gtttgcaagc agcagattac gcgcagaaaa aaggatctc aagaagatcc    3540 tttgatcttt tctacgggt ctgacgctca gtggaacgaa aactcacgtt aagggatttt    3600
ggtcatgaga ttatcaaaaa ggatcttcac ctagatcctt ttaaattaaa aatgaagttt    3660
taaatcaatc taaagtatat atgagtaaac ttggtctgac agttaccaat gcttaatcag    3720
tgaggcacct atctcagcga tctgtctatt tcgttcatcc atagttgcct gactgcccgt    3780
gtggtagata actacgatac gggagggctt accatctggc cccagtgctg caatgatacc    3840
gcgagaccca cgctcaccgg ctccagattt atcagcaata accagccag ccggaagggc    3900 cgagcgcaga agtggtcctg caactttatc cgcctccatc cagtctatta attgttgccg    3960
ggaagctaga gtaagtagtt cgccagttaa tagtttcgc aacgttgttg ccattgctac    4020
aggcatcgtg gtgtcacgct cgtcgtttgg tatggcttca ttcagctccg gttcccaacg    4080
atcaaggcga gttacatgat cccccatgtt gtgaaaaaaa gcggttagct ccttcggtcc    4140
tccgatcgtt gtcagaagta agttggccgc agtgttatca ctcatggtta tggcagcact    4200
gcataattct cttactgtca tgccatccgt aagatgcttt tctgtgactg gtgagtactc    4260
aaccaagtca ttctgagaat agtgtatgcg gcgaccgagt tgctcttgcc cggcgtcaat    4320
acgggataat accgcgccac atagcagaac tttaaaagtg ctcatcattg gaaaacgttc    4380
ttcggggcga aaactctcaa ggatcttacc gctgttgaga tccagttcga tgtaacccac    4440
tcgtgcaccc aactgatctt cagcatcttt tactttcacc agcgtttctg ggtgagcaaa    4500
aacaggaagg caaaatgccg caaaaaaggg aataagggcg acacggaaat gttgaatact    4560
catactcttc cttttcaat attattgaag catttatcag ggttattgtc tcatgagcgg    4620
atacatattt gaatgtattt agaaaaataa acaataggg gttccgcgca catttccccg    4680
aaaagtgcca cctgggtcct tttcatcacg tgctataaaa ataattataa tttaaattttt    4740 ttaatataaa tatataaatt aaaaatagaa agtaaaaaaa gaaattaaag aaaaaatagt    4800
```

-continued

```
ttttgttttc cgaagatgta aaagactcta gggggatcgc caacaaatac tacctttat    4860 cttgctcttc ctgctctcag gtattaatgc cgaattgttt catcttgtct gtgtagaaga   4920
ccacacacga aaatcctgtg attttacatt ttacttatcg ttaatcgaat gtatatctat   4980
ttaatctgct tttcttgtct aataaatata tatgtaaagt acgcttttg ttgaaatttt    5040 ttaaacctt gtttatttt ttttcttcat tccgtaactc ttctaccttc tttatttact    5100
ttctaaaatc caaatacaaa acataaaaat aaataaacac agagtaaatt cccaaattat   5160
tccatcatta aaagatacga ggcgcgtgta agttacaggc aagcgatccg tcctaagaaa   5220
ccattattat catgacatta acctataaaa ataggcgtat cacgaggccc tttcgtc      5277
```

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 17
gaactgcagc tagattccga tgctgacttg ct                                 32

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 18
tccctgcagg gttccgattt agtgctttac                                    30

ANALYSIS METHOD

Linkage mapping of genes involved in disease susceptibility and other traits in humans, animals and plants has in recent years become one of the most important engines of progress in biology and medicine. The development of polymorphic DNA markers as landmarks for linkage mapping has been a major factor in this advance. However, current methods that rely on these markers for linkage mapping in humans are laborious, allowing screening of only at most a few markers at a time. Furthermore, their power is limited by the sparsity of highly-informative markers in many parts of the human genome.

Genomic mismatch scanning (GMS) is a positional cloning strategy that has no requirement for conventional polymorphic markers or gel electrophoresis. It isolates fragments of identity-by-descent (IBD) between two related individuals based on the formation of extensive mismatch-free hybrid molecules. The GMS technique is described in U.S. Pat. No. 5,376,526, and is illustrated in FIG. 1 of the drawings accompanying this specification.

Dam methylation of one sample prior to hybridisation permits discrimination of homohybrid duplexes by virtue of methylation-sensitive restriction endonucleases that cleave only fully methylated or fully unmethylated DNA. The MutHLS methyl-directed mismatch repair proteins cleave mismatched heteroduplexes on the unmethylated strand. Except for mismatch-free heterohybrid molecules, all DNA is eliminated by a combination of Exonuclease III digestion and physical separation of single-stranded DNA using binding columns. The selected molecules are amplified by inter-Alu PCR using combinations of generic primers, and subsequently identified by hybridisation to an ordered array of DNA samples representing intervals of the genome.

Because natural polymorphisms occur on average once every several hundred bp i.e. at least once every 1000 bp, heterohybrids that are several kilobases in length and mismatch-free are likely to be IBD. Similarly, non-IBD alleles in sufficiently large heteroduplexes are likely to contain one or more mismatches and will be cleaved by the mismatch repair proteins.

The IBD maps from multiple pairs of affected relatives are combined and the resulting composite map searched for loci where genotypic concordance occurs more frequently than would be expected by chance. These loci represent candidate regions that may harbour the target mutation(s).

The relative recovery of DNA from a locus when the two genomes share an allele IBD compared to the recovery from that locus when the two genomes are not IBD dictates the reliability of the technique. For analyses involving human genomic DNA, enrichment by a factor of 1–2 for 50% of IBD fragments and by a factor of 2–5 for 35% of IBD fragments has been reported. Only 15% of IBD fragments are reported to be enriched by a factor of >5. Furthermore, the yield of DNA after GMS selection is very poor such that amplification of the selected fragments prior to hybridisation to the array is required.

Enrichment of Fragments of IBD in Two Individuals with Common Ancestry.

It is one object of the present invention to provide novel methods of performing genetic analysis to obtain enrichment of fragments of IBD. Thus in one aspect this invention provides a method of performing genomic analysis by:
a) digesting genomic DNA to be compared from two different sources to provide genomic fragments whose average length is greater than the average spacing between natural polymorphisms;
b) combining under hybridisation conditions single strands of the genomic fragments from the two sources;
c) separating heterohybrids from homohybrids; and
d) separating mismatch-free heterohybrids from hybrids with mismatches;
which method comprises ligating an adapter to each end of each genomic fragment produced in step a), said adapter being, in double-stranded mismatch-free form, resistant to nuclease digestion.

The method involves comparing genomic DNA from two different sources, generally two different viral or prokaryote or eukaryote (e.g. human, animal or plant) individuals who share a particular phenotype which may have been acquired from a common ancestor. Phenotypes are observable or measurable characteristics displayed by an organism under a particular set of environmental and/or genetic influences. Hybridisation conditions may depend on the genomic fragments being analysed and will be well known to the skilled reader. As noted, natural polymorphisms occur in human genomic DNA on average once every several hundred bp i.e. at least once every 1000 bp. The genomic DNA of the two individuals to be compared is cut into fragments that are in general longer than this. Thus each genomic fragment contains on average one or more polymorphisms. This may be effected by use of a restriction enzyme (or two or more restriction enzymes) that cuts relatively infrequently. Suitable restriction enzymes include those of type II and also those of type IIS. It would alternatively be possible to effect restriction of the genomic DNA by physical or chemical as opposed to enzymatic means.

An adapter is ligated to each end of each fragment. An adapter is an at least partly double-stranded polynucleotide, generally oligonucleotide, having if required an overhang complementary to the overhang generated by the restriction enzyme. Alternatively, both the fragments and the adapter may have blunt ends for ligation. The adapters may comprise oligonucleotides of an arbitrary sequence that does not render them prone to secondary structure, liable to hinder efficient ligation, amplification, or selection on the basis of mismatch discrimination. Primers, comprising all or part of an adapter sequence, used for amplifying DNA under analysis, are further examined to ensure non-specific amplification is avoided. When in double-stranded mismatch-free form, the adapter is resistant to nuclease digestion, that is to say more resistant than is ordinary DNA. Such resistance can be conferred by providing modified internucleotide linkages e.g. phosphorothioate or methylphosphonate linkages, or by the use of nucleotide analogues that confer nuclease resistance. Preferably however a first adapter ligated to fragments of genomic DNA from the first source contains a mismatch; and a second adapter ligated to fragments of genomic DNA from the second source also contains a mismatch; the two adapters being so designed that the forward strand of one adapter will hybridise to the backward strand of the other adapter to form a mismatch-free heterohybrid. A heterohybrid comprises two strands from different individuals and is contrasted with a homohybrid which comprises two strands from the same individual. The two systems are described in more detail below with reference to FIGS. 2 and 3 of the accompanying drawings, in which:

FIG. 2 shows the use of two adapters each having a mismatch within a section comprising phosphorothioate linkages; and FIG. 3 shows the use of two different adapters each having a mismatch outside a section having phosphorothioate linkages.

The modified method for affected-pair analyses involves restriction digestion of both genomic DNA samples and ligation of adapter sequences to each. These adapters contain mismatched regions that persist after hybridisation in the homoduplex molecules. By contrast, the adapter sequences are fully complementary in heteroduplexes. Subsequent use of a mismatch recognition protein e.g. T4 endonuclease VII and nuclease digestion results in the elimination of all molecules possessing mismatches. Mismatch-free heteroduplex molecules are resistant to digestion e.g. due to the inclusion of phosphorothioate or methyphosphonate linkages in the adapter sequences that convey protection. These molecules can be amplified efficiently and conveniently with a single primer pair prior to analysis as discussed below.

The ligation of adapters to all fragment ends provides a convenient opportunity to selectively digest homohybrid molecules that are produced by hybridisation of the two DNA samples, and to amplify efficiently the enriched fragments with an appropriate adapter primer. The presence of phosphorothioate or methyphosphonate linkages, or other inhibitory features, at the adapter's ends provides protection against nuclease digestion. The adapter sequences are designed judiciously to be fully complementary on formation of heterohybrid molecules. In homohybrid molecules, however, the mismatch persists. Strand cleavage of the mismatch at a position proximal to the phosphorothioate or methyphosphonate linkages creates vulnerability to subsequent nuclease digestion and culminates in the elimination of the homohybrid molecules. Phosphorothioate or methyphosphonate protection in heterohybrid molecules persists, however, since strand cleavage does not occur in the absence of a mismatch.

A number of types of mismatched adapter would be appropriate for this purpose and include 'Y' shaped adapters with non-complementary ends (FIG. 2), and adapters with one or more mismatched nucleotides at a position along the adapter's length (FIG. 3). In the former case, a single strand specific endonuclease may be used to achieve strand cleavage, while T4 endonuclease VII would cleave the mismatch in the latter case. If a 3'-5' exonuclease is used subsequently to digest the cleaved molecules, oligonucleotide phosphorylation is necessary to ensure that both adapter strands form covalent bonds with each genomic fragment. However, if a 5' to 3' exonuclease is employed this may not be necessary. The use of mismatched adapters for selective elimination of homohybrid duplexes as an inherent feature of the mismatch discrimination procedure obviates the need for dam methylation of one genomic sample and subsequent digestion of the hybrid molecules by methylation sensitive restriction enzymes.

Strand scission by the MutHLS mismatch recognition proteins (as used in U.S. Pat. No. 5,376,526) has an absolute requirement for at least one (GATC) site within the mismatched duplex that should be at least 150 base pairs from the fragment end to achieve maximal activity. Only the unmethylated strand is cleaved in a hemimethylated duplex, and the efficiency of this depends on the nature of the mismatch and the context of the surrounding sequence. The enzyme system fails to recognise C•C mismatches and insertion/deletion loops of more than four nucleotides. By contrast, T4 endonuclease VII is a mismatch recognition protein that is capable of discriminating all single base mismatches as well as insertion/deletion loops of all sizes. Fragments up to 4kbp have been digested successfully and maximal efficiency of cleavage is achieved when the mismatch is separated from a fragment end by at least nine nucleotides. Suitable buffers include Tris, pH 8, and more preferably phosphate buffers. Although sequence context and the nature of the mismatch also affects the efficiency of T4 endonuclease VII digestion, significant benefits may be achieved by replacement of the MutHLS proteins with this enzyme. Other mismatch recognition/repair proteins may be suitable including Cel1 and T7 endonuclease I. The choice of methods for separation of mismatched fragments from matched fragments is not limited to the use of enzymes, but may also be accomplished by chemical or physical means.

It is likely that elimination of cleaved duplexes by nuclease digestion will be more efficient than relying on their physical separation with single stranded DNA binding columns. One or more enzymes that provide single-strand specific endonuclease activity and either 5'-3' or 3'-5' exonuclease activity may be appropriate. In addition, since T4 endonuclease VII may in some circumstances create single strand scission, it is important that the exonuclease is active at a nick. Furthermore, in order to preserve the heteroduplex molecules, the exonuclease must be inhibited by phosphorothioate or other modified linkages. Suitable candidates for use either singularly or in combination include, but are not limited to, Bal3I nuclease, S1 nuclease, Mung bean nuclease, T7 gene 6 exonuclease, Exonuclease III and the 3'-5' exonuclease activity of polymerases, such as T4 DNA polymerase.

Selective Enrichment of Common Sequences in Pooled Samples: Enrichment of Fragments IBD in the Pooled Genomes of Individuals with Common Ancestry Identification of candidate disease loci using the existing GMS method typically requires the analysis of more than 200 affected pairs and the hybridisation of the enriched fragments to an array of genomic clones. The candidate region is determined by scrutiny of the composite map of enriched fragments, constructed from the cumulative data of all affected-pair analyses, and identification of regions where genotypic concordance occurs more frequently than would be expected by chance.

The need for the numerous separate pair-wise analyses and subsequent hybridisation steps could be avoided if a large number of affected individuals was analysed en masse. Accurate diagnosis of phenotype would be an important preliminary step. However, provided that the same sequence variant was common to all, e.g. because all, or the majority, of the affected individuals had acquired their phenotype through common ancestry, a candidate region could be identified in a single analysis.

It is another object of this invention to meet this need. In this aspect the invention provides a method of performing genomic analysis by:

i) providing genomic DNA, pooled from a plurality of individuals that share a phenotype;

ii) digesting the genomic DNA to provide genomic fragments whose average length is greater than the average spacing between natural polymorphisms;

iii) ligating an adapter to each end of each genomic fragment produced in step ii), said adapter being, when in double-stranded mismatch-free form, resistant to nuclease digestion;

iv) denaturing and re-annealing the mixture of adapter-terminated genomic fragments produced in step iii);

v) removing from the mixture produced in step iv) hybrids containing mismatches and if required amplifying mismatch-free hybrids;

vi) and repeating steps iv) and v) to recover one or a few mismatch-free hybrids associated with the phenotype.

Reference is directed to the accompanying FIG. 4 which is a diagram showing this technique.

A suitable protocol involves the pooling of genomic DNA samples of affected individuals e.g. of presumed common ancestry and restriction digestion of the genome pool. A single adapter, comprising complementary oligonucleotides that convey phosphorothioate or methylphosphonate or other protection, is ligated to all fragments prior to denaturation and re-annealing of the pool. Provided that a large number of individuals contributed to the pool, most fragments will form heteroduplexes on hybridisation. Mismatched molecules are eliminated by use of a mismatch repair protein e.g. T4 endonuclease VII and nuclease digestion. The remaining molecules are amplified using a single primer appropriately designed to complement the adapter sequence. The amplified products are subjected to reiterated rounds of mismatch discrimination, resulting in depletion of mismatched heteroduplex molecules and enhanced enrichment of IBD fragments. The number of cycles may depend on the number and similarity (or relatedness) of the individuals involved. Finally, the selected fragments may be analysed further e.g. by hybridisation to reference sequences of nucleic acid. Alternatively, if the enrichment of IBD fragments by reiterated mismatch discrimination is sufficient to effectively exclude all non-informative fragments, the selected molecules may be directly cloned and sequenced. In addition to eliminating the need for multiple affected-pair analyses, therefore, the requirement for an array of genomic clones would be abolished.

In another aspect, this invention provides a set of four oligonucleotides, wherein each oligonucleotide of the set: is complementary to a first other oligonucleotide of the set and forms therewith a hybrid that is resistant to nuclease digestion; and is substantially complementary to a second other oligonucleotide of the set. Preferably each oligonucleotide comprises one or more phosphodiester bonds selected from phosphorothioate and methylphosphonate.

In another aspect, this invention provides a kit for performing a method as defined, which kit comprises this set of four oligonucleotides together with a ligase and a nuclease.

Selective Enrichment of Common Sequences by Subtractive Hybridisation of Affected and Wild Type Genomic Fragments Using the original GMS method, large tracts of identical-by-descent DNA can be enriched. Considerable effort is required subsequently to analyse these candidate sequences and identify any sequence variants that they may contain. The larger the candidate sequences, the greater is the effort required to scrutinise them for sequence variants. A method that generates very short candidate sequences, therefore, will provide considerable advantage. Moreover, the method would be especially suited to the analysis of all sequence differences in both DNA and RNA.

It is another object of this invention to meet this need. In this aspect the invention provides a method of performing genomic analysis by:

i) providing first nucleic acid, pooled from a plurality of individuals that share a phenotype;

ii) digesting the said first nucleic acid to provide fragments who's average length is about equal to or less than the average spacing between natural polymorphisms;

iii) ligating an adapter to each end of each fragment produced in step ii) to form adapter-terminated nucleic acid fragments which are, when in double-stranded mismatch-free form, resistant to nuclease digestion;

iv) denaturing and re-annealing the mixture of adapter-terminated nucleic acid fragments produced in step iii);

v) removing from the mixture produced in step iv) hybrids containing mismatches and if required amplifying mismatch-free hybrids;

vi) repeating steps iv) and v) to recover a first mixture of mismatch-free hybrids;

vii) providing second nucleic acid pooled from a plurality of individuals that do not share the same phenotype;

viii) subjecting the nucleic acid of vii) to the said steps ii) to vi) to recover a second mixture of mismatch-free hybrids;

ix) combining under hybridisation conditions single strands of the said first mixture of mismatch-free hybrids and the said second mixture of mismatch-free hybrids;

x) and recovering nucleic acid fragments that do not form mismatch-free hybrids and are associated with the phenotype.

Step ii) may be effected by the use of at least one restriction enzyme that cuts relatively frequently. Thus the majority of fragments will not contain any natural polymorphism.

Reference is directed to FIG. 5 which is a diagram showing this technique.

If the genomes of affected individuals are restricted with one or more enzymes that cleave nucleic acid frequently, a pool of very short fragments will result. The number fragments generated in this way will exceed the total number of polymorphic sequences within the genome. As such, when dissociated and allowed to re-anneal, most fragments will form perfectly matched heteroduplex molecules. It is preferred to have as close to one polymorphism per restriction fragment, but preferably no more, as achievable. With smaller fragments the proportion of identical fragments that contribute 'noise', from which the informative fragments mismatched between the two pools must be differentiated, in the method increases. With larger fragments the proportion of fragments with greater than one polymorphism increases and hence the likelihood of losing fragments that contain the informative sequence change: because the neighbouring polymorphism(s) in the same fragments may not be identical in the pool of individuals.

A single adapter, containing phosphorothioate or methylphosphonate linkages to provide protection to nuclease digestion, is ligated to all nucleic acid fragments. These fragments are dissociated and re-annealed, and mismatched molecules are cleaved by a mismatch repair protein e.g. T4 endonuclease VII. The cleaved molecules are eliminated by one or more nucleases that provide endonuclease and 5' to 3' or 3' to 5' exonuclease activities. This process of strand dissociation and re-annealing, followed by mismatch discrimination using T4 endonuclease VII and appropriate nucleases is reiterated.

Nucleic acid of wild type individuals is pooled, restricted, ligated to adapters and subjected to reiterated mismatch discrimination, in a similar manner to that of the affected individuals. In each separate pool, therefore, only fragments that contain sequences common to all individuals in the pool should persist.

The enriched fragments of the affected pool are hybridised to an excess of the enriched fragments of the wild type pool. Provided that the individuals contributing nucleic acid to each pool were taken from the same population e.g. who share the same ethnic origin, the vast majority of fragments should form perfectly matched duplexes. Only the fragment that harbours the causative mutation distinguishing the phenotypes should form a mismatched duplex on hybridisation. These mismatched molecules are selected. Completion of the protocol, therefore, culminates in very short genomic fragments potentially containing the sequence variant of interest. These selected fragments can then be analysed with relative ease, e.g. by hybridisation to reference sequences of nucleic acid, to identify the informative sequence change.

The methods described above are preferably carried out with genomic DNA that represents part or all of a genome. A genomic subset may be generated for analysis by one of a number of approaches known to the skilled individual including, but not limited to, selective amplification by techniques such as interAlu-PCR, or confining an analysis to fragments, produced by restriction enzyme digestion, that lie within a predefined size range. A fraction of the genome to be analysed may be selected on the basis of expression in tissues of interest. In this instance mRNA may first be converted to cDNA using conventional methods prior to analysis as described above. Alternatively, RNA may be subjected to analysis as described above.

Cloning and sequencing is the preferred method for analysing sequences that remain at the end of the methods. It is, however, also possible to perform this analysis by hybridisation to reference sequences of nucleic acid including genomic DNA, cDNA or oligonucleotide representations thereof. Examples include hybridisation to arrays of nucleic acid sequences comprising of BAC or cDNA clones, oligonucleotides or chromosomes (See Boyle, et al. (1990) *Genomics* 7:127–130; Lichter, et al. (1990) *Proc. Natl. Acad. Sci. USA* 87:6634–6638; Schena, et al. (1995) *Science* 270:467–470; Lockhart, et al. (1996) *Nature Biotechnology* 14:1675–1680).

BRIEF DESCRIPTION OF THE DRAWINGS

Reference is directed to the accompanying drawings in which.

Figure 1:
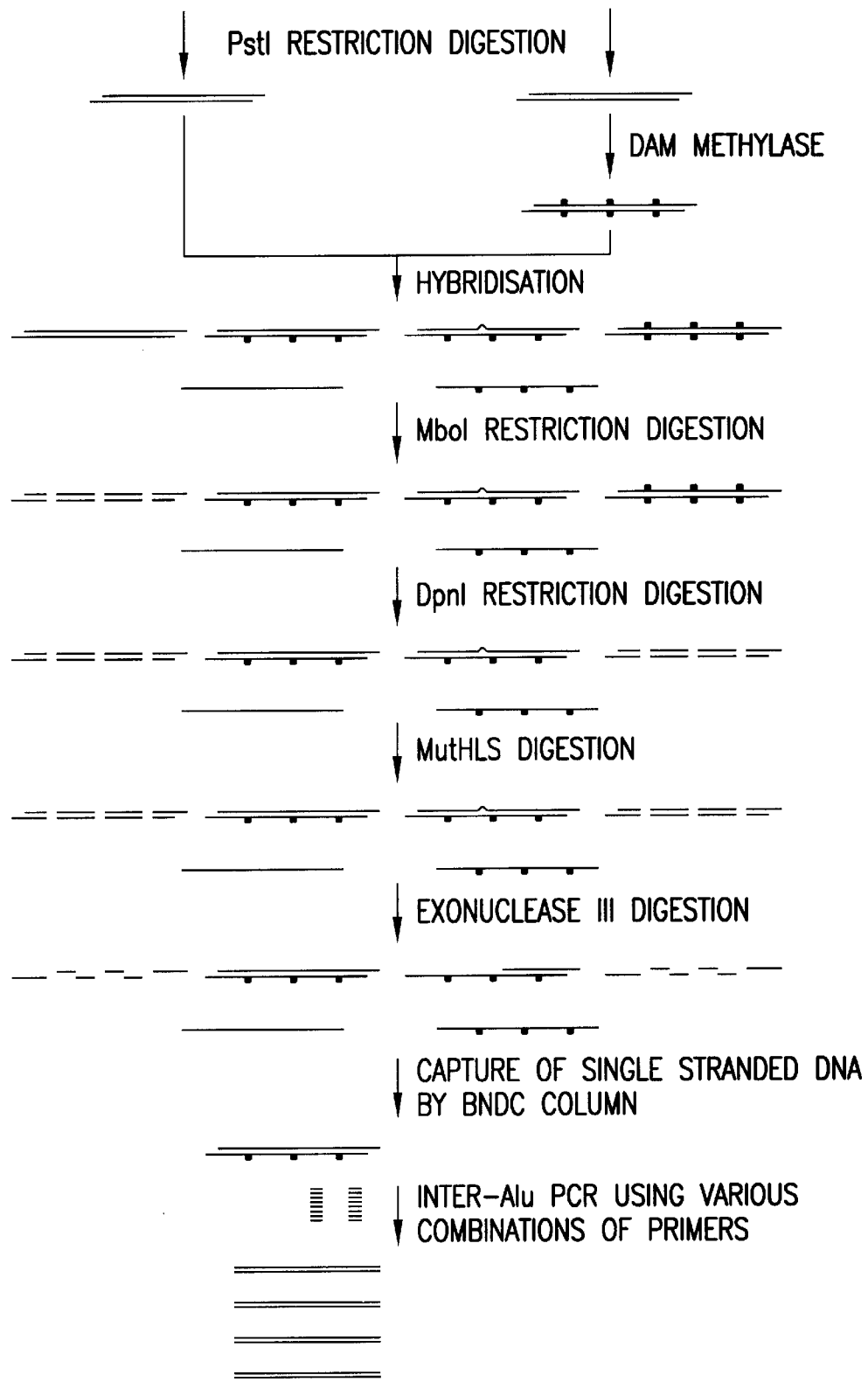
FIG. 1 is a diagram of the known GMS system, entitled "Enrichment of fragments identical-by-descent (IBD) in two individuals of common ancestry".
Figure 2:
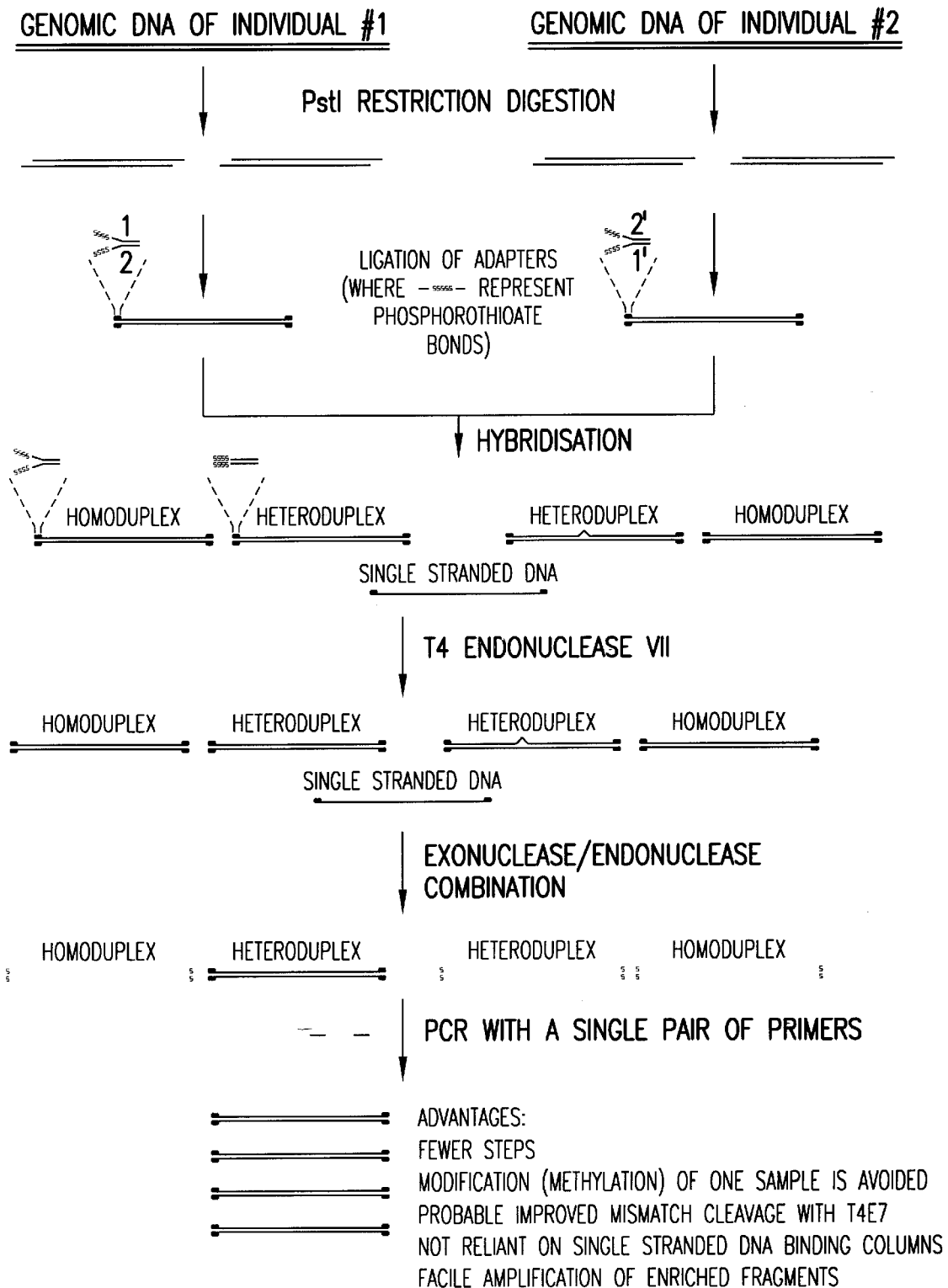
Figure 3:
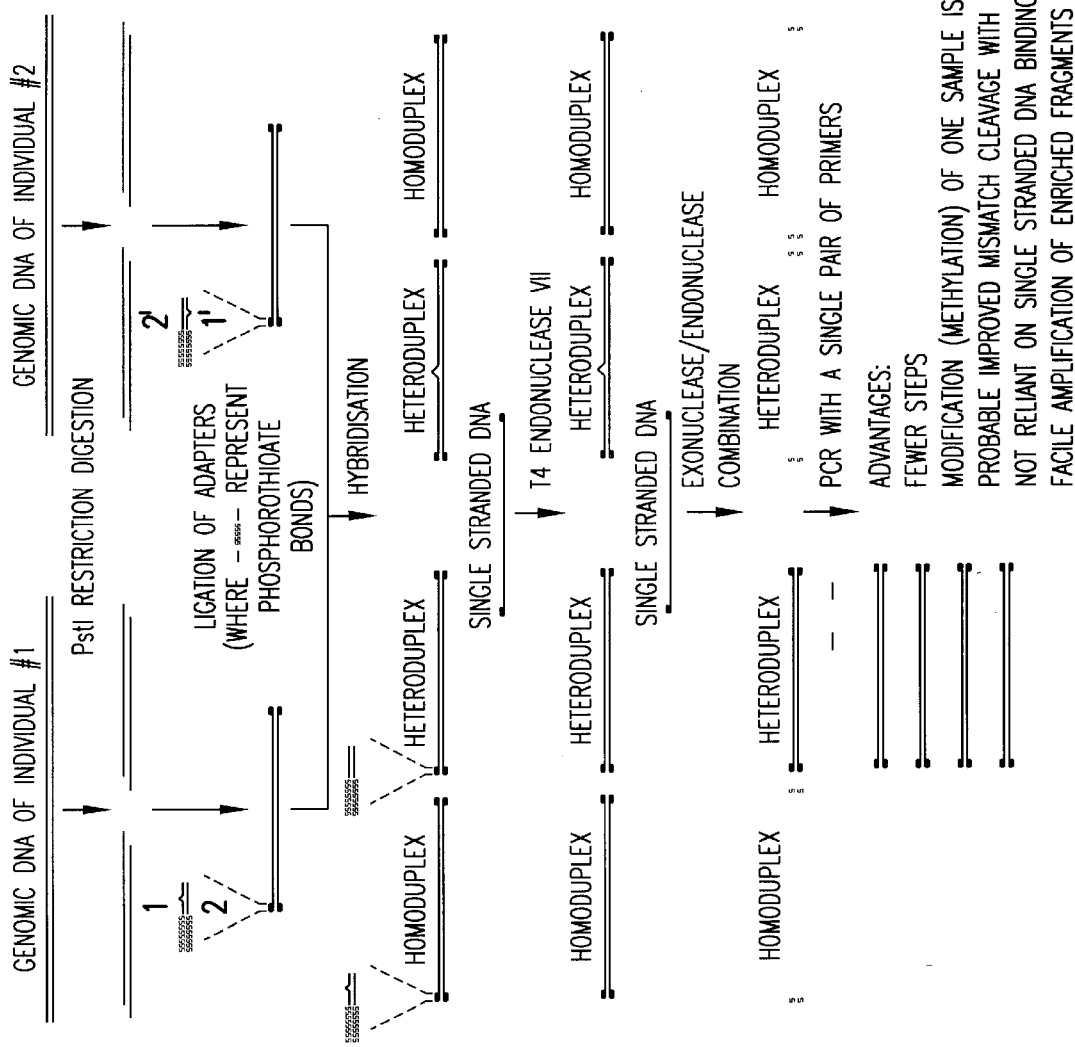

Each of FIGS. 2 to 5 is a diagram of a different genomic analysis method described herein. Each of FIGS. 2 and 3 is entitled "Enrichment of fragments IBD in two individuals with common ancestry".

Figures 4A, 4C:
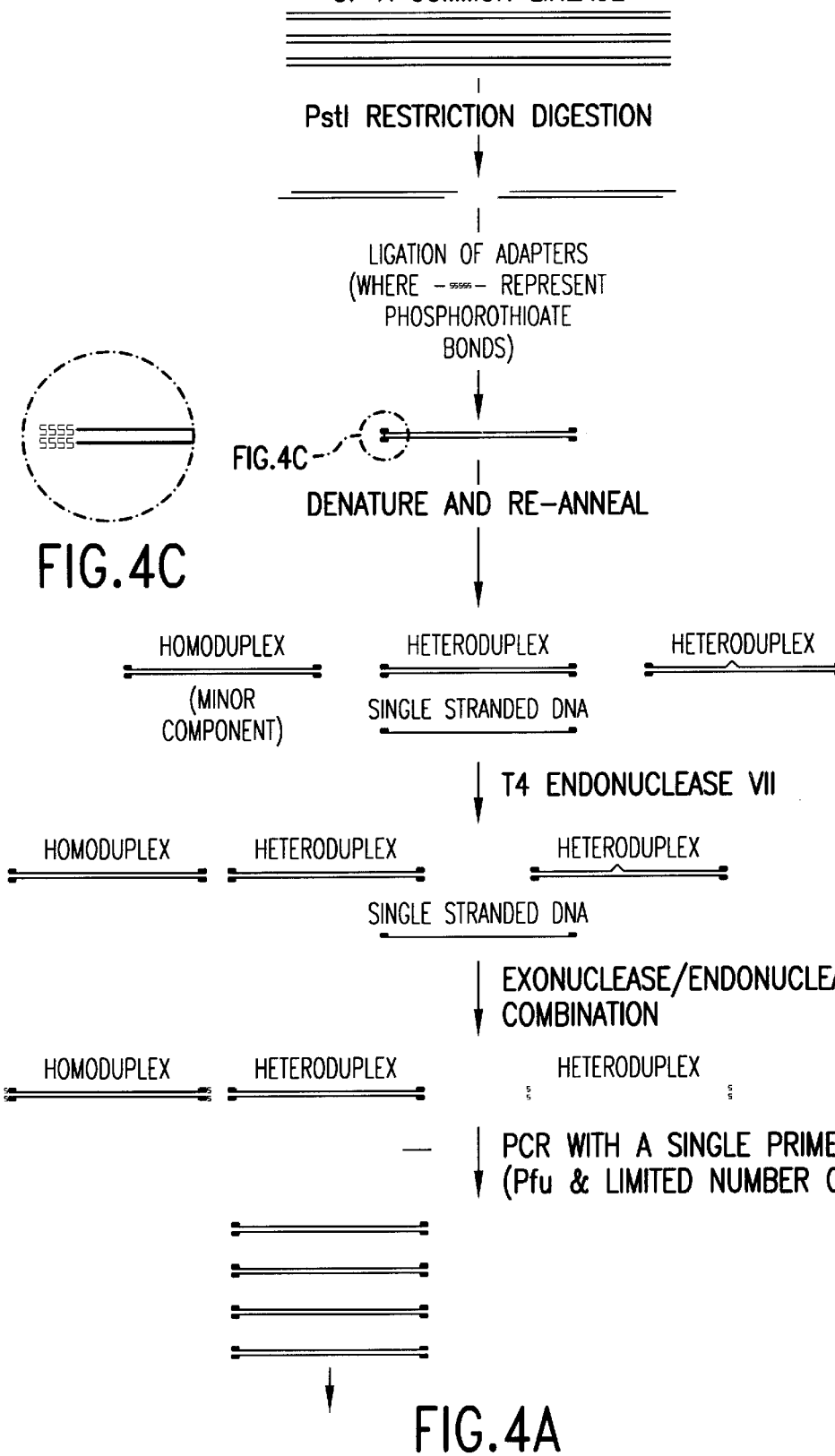
Figure 4B:
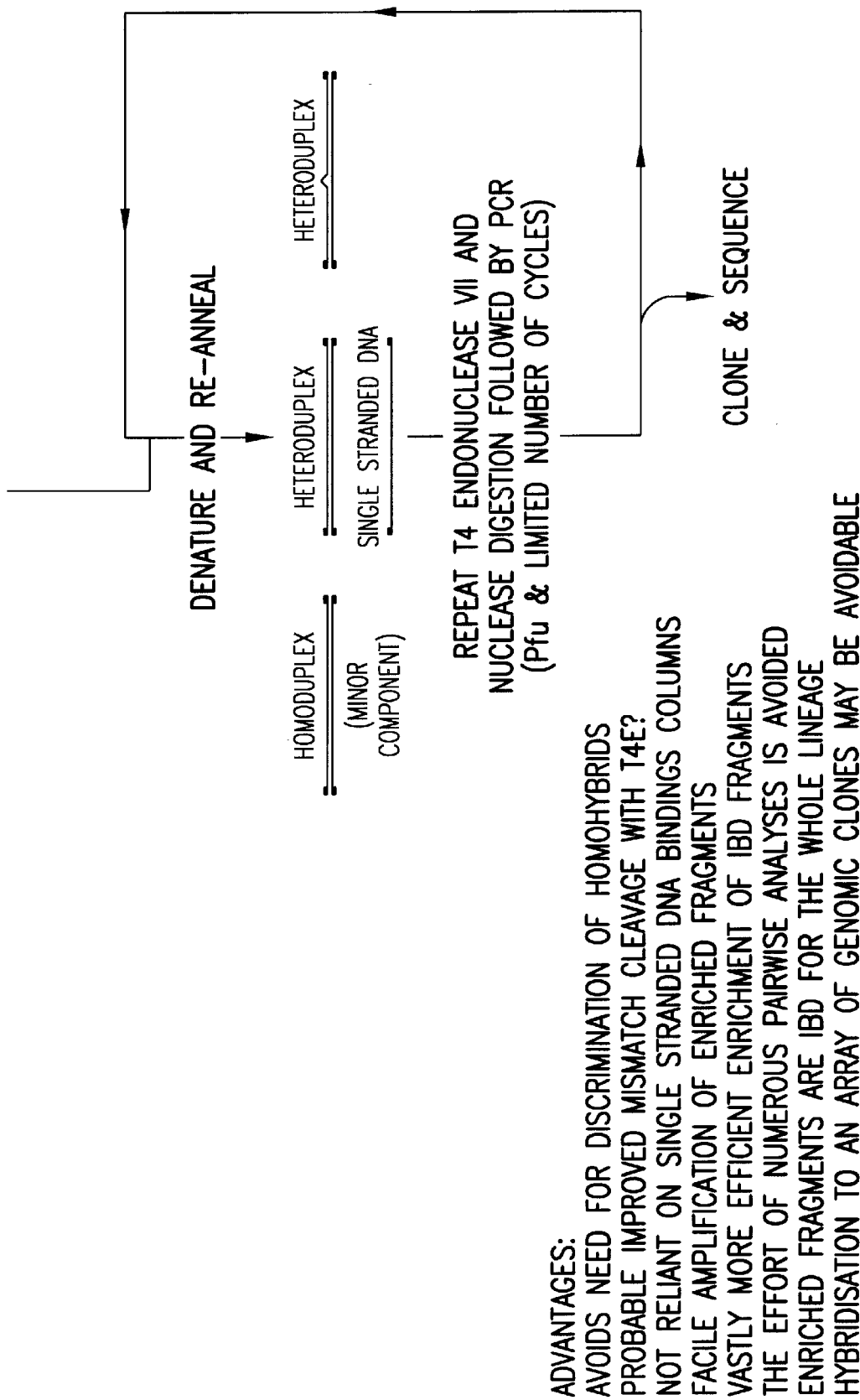

FIG. 4 is entitled "Enrichment of fragments IBD in the pooled genomes of individuals with common ancestry".

Figure 5:
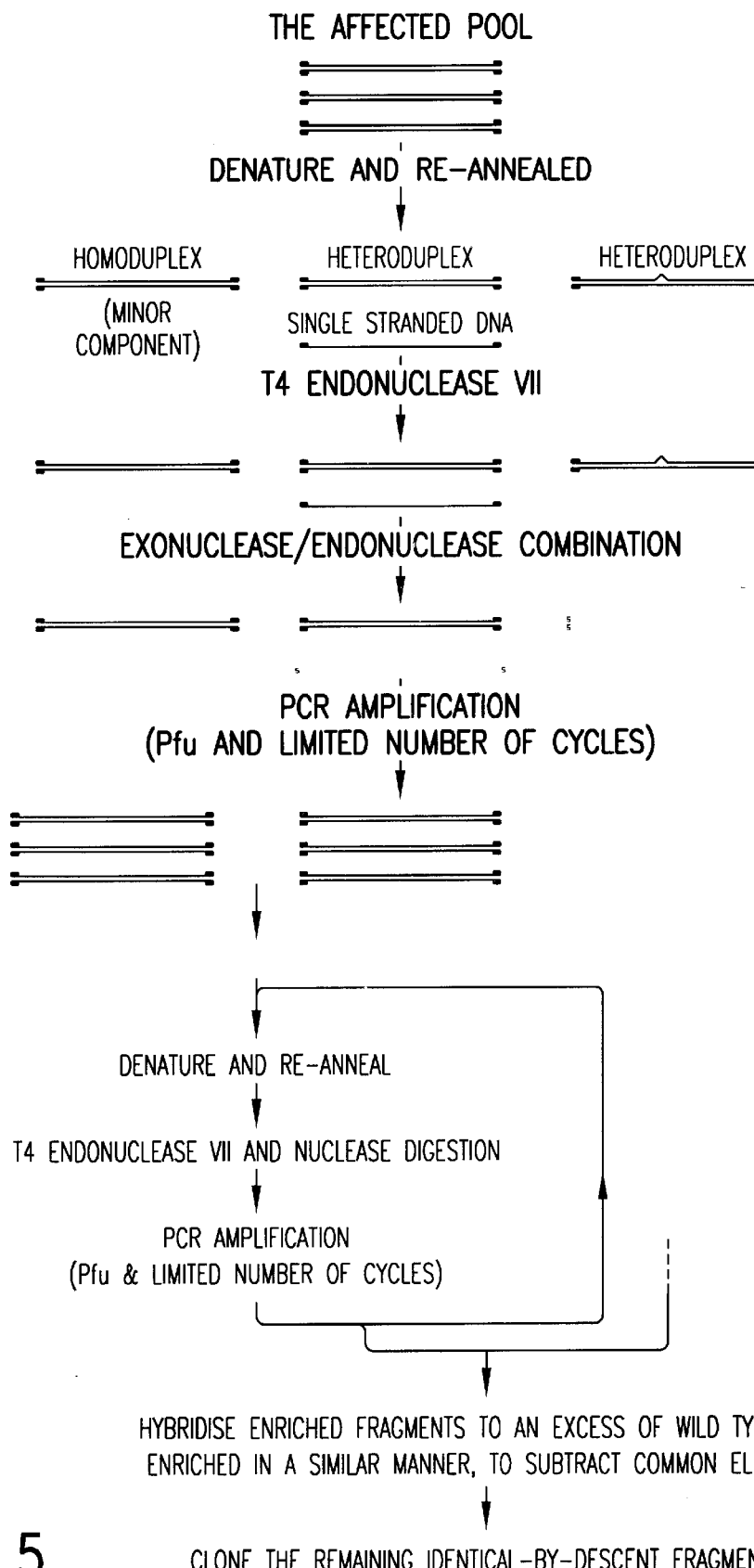

FIG. 5 is entitled "Subtractive enrichment of informative fragments using pooled nucleic acid of affected and wild-type individuals".

Figure 6:
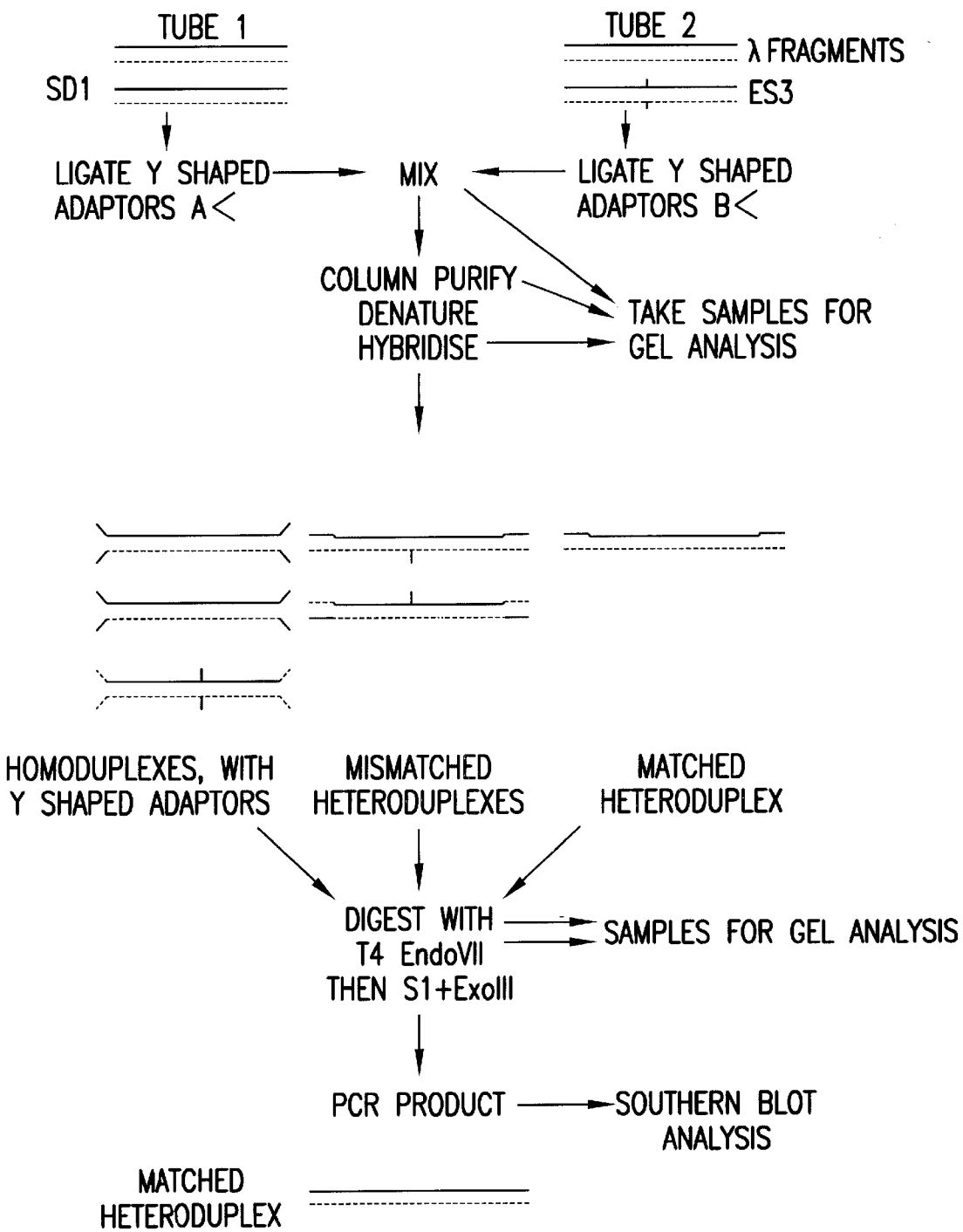

FIG. 6 is a diagram of the system used in Example 3.

Figure 7:
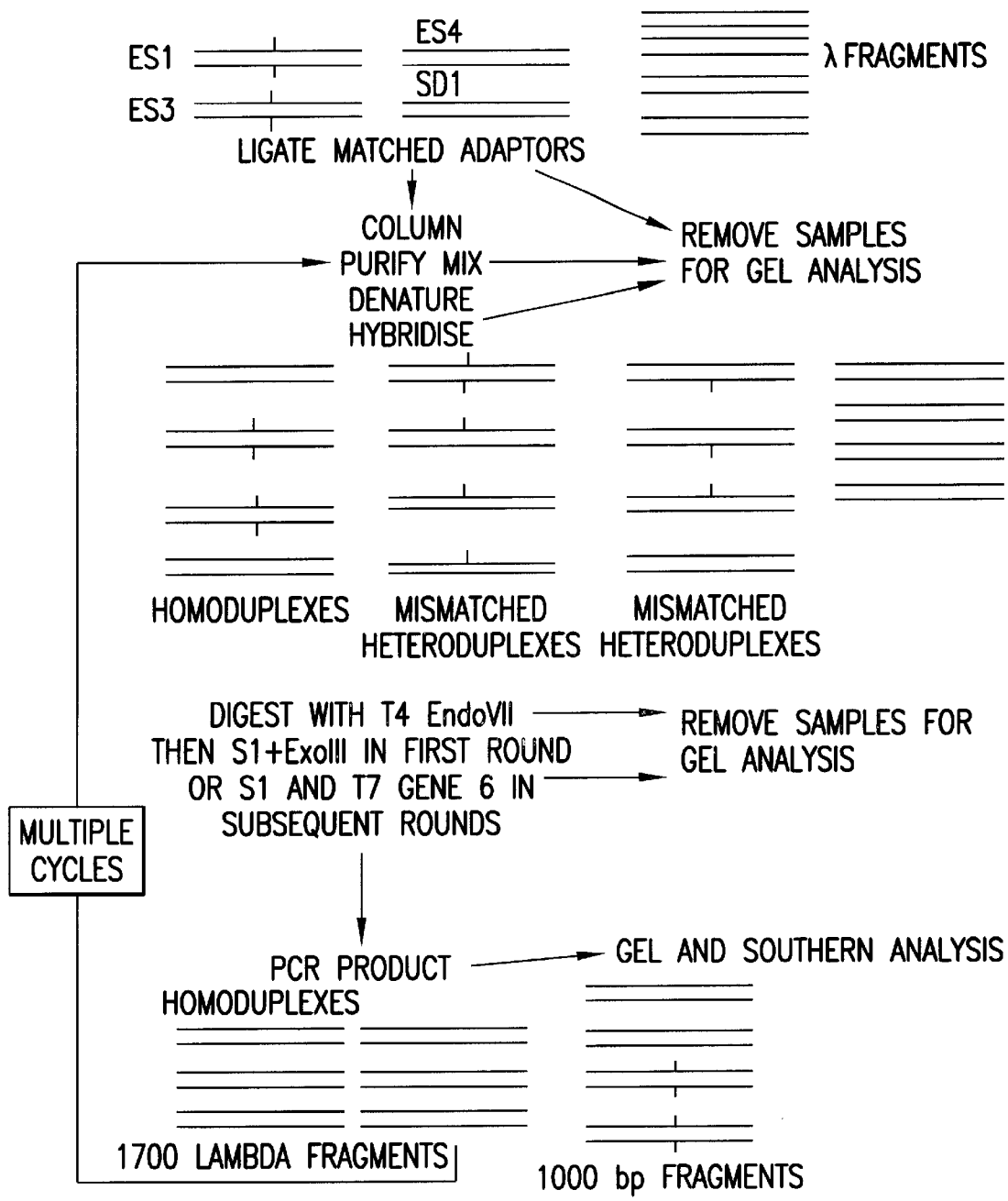

FIG. 7 is a diagram of the system used in Example 4.

In the experimental section which follows, Examples 1 and 2 show the preparation and characterisation of different sets of four oligonucleotides according to the invention. Examples 3 and 4 relate to genomic analysis methods according to the invention, performed using combinations of those oligonucleotides as adapters.

EXPERIMENTAL DATA

EXAMPLE 1

Four oligonucleotides were synthesised [Genosys Biotechnologies (Europe) Ltd.] for ligation to PstI digested DNA that would allow selective elimination of homohybrid molecules by nuclease digestion while heterohybrid duplex DNA remained intact. Where appropriate, phosphorylation (phosphate-) and phosphorothioate linkages ($_s$) were included in the synthesis of each oligonucleotide. The sequences were as follows:

Oligo A: $C_sA_sT_sT_s$CGGATGTTGATCGCGGC-CGCTTGTCTGCA (SEQ ID NO: 1)

Oligo B: 5' Phosphate-GACAAGCGGCCGCGATCAAGTAGGC$_sT_sT_sA_sC$ (SEQ ID NO: 2)

Oligo C: 5' $G_sT_sA_sA_s$GCCTACTTGATCGCGGC-CGCTTGTCTGCA (SEQ ID NO: 3)

Oligo D: 5' Phosphate-GACAAGCGGCCGCGATCAACATCCG$_sA_sA_sT_sG$ (SEQ ID NO: 4)

Oligos A+D and oligos B+C are complementary, whereas oligos A+B and oligos C+D are only partially complementary.

If oligos A+B were annealed and ligated to PstI digested DNA a mismatched adapter would result at each fragment end. Similarly, mismatched adapters could be ligated to another source of PstI digested DNA if oligos C+D were annealed. Hybridisation of the two sources of digested and differentially ligated DNA, therefore, would result in homoduplex molecules possessing mismatched adapter sequences and heteroduplexes for which the adapters were mismatch-free. Subsequent nuclease digestion would selectively eliminate the homoduplex DNA, while heteroduplex molecules retained their phosphorothioate protection and remained intact.

To investigate the effect of matched and mismatched adapters on nuclease digestion, plasmid DNA was digested to completion using PstI [Amersham Pharmacia Biotech] and microconcentrated [Microcon-30: Amicon]. Adapters were prepared by combining oligos A+B or oligos A+D in equimolar amounts and incubating them in 1×T4 DNA ligase buffer [Amersham Pharmacia Biotech] for 1 hour over a range of temperatures from 50° C. to 10° C. With adapter in a 50×molar excess, PstI digested DNA was ligated to each adapter type by overnight incubation at 16° C. in the presence of T4 DNA ligase. In each case, the adapter-ligated plasmid DNA was gel purified [QIAquick Gel Extraction Kit: Qiagen] prior to nuclease digestion. At a concentration of 35 ng/µl, each of the two gel purified DNAs were subjected to Bal31 nuclease [Amersham Pharmacia Biotech] digestion under a variety of reaction conditions. It was found that incubation at 20° C. for 40 minutes in the presence of 0.2 units/µl Bal31 nuclease resulted in digestion of the DNA ligated to mismatched adapters, while that ligated to mismatch-free adapters was resistant to nuclease attack. It was concluded, therefore, that it would be feasible to selectively eliminate homoduplex molecules from a mixture containing heteroduplex DNA using appropriately designed adapters.

EXAMPLE 2

Demonstrating Nuclease Resistance Conferred by the Presence of Methyl Phosphonate Linkages and Their Utility in Selecting Fragments Bearing non-Mismatched Adapters.

Exonuclease III and S1 will digest linear DNA fragments. The following experiment was performed to demonstrate the protection from enzymatic digestion conferred on DNA by methylphosphonate modified adapters. All reagents in this and subsequent examples were from Amersham Pharmacia Biotech unless otherwise stated.

Primer I and primer J (obtained from Genosys) were used to amplify a 129 bp dog genomic DNA fragment, 31A, that had been cloned into plasmid pT3/T7. These primers also amplified short stretches of plasmid sequences flanking the insert. PCR amplification was performed in the presence of 100 pmol of each primer I and J, 1.5 mM $MgCl_2$, 0.2 mM dNTPs, 2.5 units of Taq polymerase and 1×Taq reaction buffer in a final volume of 100 µl. $^{33}$P-dATP was included in the PCR-reaction to internally radiolabel the amplification product. The resulting amplified fragment of 185 bp was purified with GFX-PCR purification kit and the amount of DNA was quantified on an 1% agarose gel using Vistra Green™ staining.

Primers I and J (Genosys) were as follows:
Primer I: 5' p-GTTTCTTCTGCAGGTCGACTCTAGAGGA 3' (SEQ ID NO: 5)
Primer J: 5' p-GTTTCTTCTATAGGGAATTCGAGCTCGG 3' (SEQ ID NO: 6) Fragment 31A: 5' CACTTGGGACTTTGGATTGGTCACTACT-GACATTTTGTATGCAGCAGC CACCTGTTCTG-GTGTGTGTGTGTGTGTGTGTGTGTGTGT-GTGTGTCTT GTTTGTTTTAATGCAAGCAAGAATG-GAAACAAAGAC 3' (SEQ ID NO: 7)

PCR-amplification with Taq polymerase results in the addition of extra A-residues to the 3' ends of the amplified molecules. This property was utilized to create complementary ends on the amplified fragment 31A for adapters KL and KM. The adapter KL was formed by annealing together oligonucleotides K and L, which are partially complementary at one end to permit ligation, but mismatched at the other end, and when annealed together will form a 'Y' shaped structure. Annealing oligonucleotides K and M, which are fully complementary to each other results in non-mismatch adapter KM. In both adapters a 1 bp overhang exists that is complementary to Taq-amplified DNA fragments.

The oligonucleotides K, L and M (Interactiva Biotechnologie GmbH) were as follows:
Oligonucleotide K: 5' AAAGCCTACAACTAGCCGTC-CGCTTGTCT 3' (SEQ ID NO: 8)
Oligonucleotide L: 5' GACAAGCGGACGCGATCAACATCC655A 3' (SEQ ID NO: 9)
Oligonucleotide M: 5' GACAAGCGGACGGCTAGTTGTAGG788T 3' (SEQ ID NO: 10)

Where 5 represents dA-methylphosphonate
6 represents dG-methylphosphonate
7 represents dC-methylphosphonate
8 represents dT-methylphosphonate A 20-fold molar excess of adapters KL and KM were separately ligated with 64 ng of PCR-amplified fragment 31A. These reactions were performed at 37° C. for 2 hours in the presence of 1×ligase buffer and 1 unit of T4 ligase in a volume of 10 µl.

The success of ligation was verified by analyzing 1 µl aliquots of ligation reactions on a 6% denaturing polyacrylamide-gel. The gel was fixed in 10% acetic acid, dried and exposed to a phosphor screen. As compared to unligated fragment 31A, both ligation reactions resulted in the appearance of fragments that had a higher molecular weight, which corresponded to increase in size by 56 bp, i.e. the combined length of two adapters. This confirmed that 31A-fragments were successfully ligated to an adapter at both ends.

Both adapters KL and KM have three methylphosphonate linkages in the 3' end that does not participate in the ligation event. The ability of these linkages to protect against digestion by Exonuclease III and S1 nuclease was analyzed as follows. Fragments 31A were either ligated to mismatch-containing Y-shaped adapter KL, to non-mismatch containing adapter KM, or that were free of adapters, were independently incubated at 37° C. for 60 minutes with 10 units of Exonuclease III and 25 units of S1 nuclease in a buffer containing 50 mM Tris-HCl pH 7.5, 20 mM $MgCl_2$ and 50 mM NaCl at a final volume of 10 µl. The reactions were stopped by adding 4 µl of stop solution containing 20 mM EDTA, 95% formamide, 0.01% bromphenol blue and 0.01% xylene cyanol. Aliquots of 7 µl were analyzed on a 6% denaturing PAGE gel. The gel was fixed in 10% acetic acid, dried and exposed to a phosphor screen.

The results showed that 31 A-fragments that had been ligated at both ends with adapter KM were the only ones to survive the digestion. This result demonstrates that DNA fragments can be protected from Exonuclease III and S1 nuclease digestion by ligating them to adapters that contain 3' methylphosphonate linkages.

A similar strategy was used separately to demonstrate that by including methylphosphonate linkages in the 5' end of the adapters, the DNA fragments could be protected against digestion by T7 gene 6-product.

Model System Used in Example 3 (FIG. 6) and Example 4 (FIG. 7)

DNA fragments were used to demonstrate the enrichment of a common fragment relative to fragments which contain mismatches from two populations of DNA (example 3) or one pool of DNA (example 4). The fragments were spiked into a background of human genomic DNA or E.coli genomic DNA. The use of spikes avoided the extensive genotyping that would have been required if two different genomes from the same organism had been compared, and also facilitated the analysis of the experiments. The examples below utilised the recognition of a single base mismatch in a DNA duplex.

The fragments used were as follows (the sequences are shown in appendix 1):
1. A 1700 bp PstI fragment excised from lambda.
2. A 1000 bp fragment amplified by PCR from a plasmid pSD1.
3. A 1000 bp fragment amplified by PCR from a plasmid pES3, where pSD1 and pES3 differed only by a single base change of G to C, 200 bases from the 5' end of the fragment.
4. A 1000 bp fragment amplified by PCR from a plasmid, pES4, where ES4 differed from SD1 and ES3 by a single base deletion 200 bases from the 5' end of the fragment.
5. A 1000 bp fragment amplified by PCR from a plasmid, pES1, where ES1 differed from SD1 by a single base change of G to A 200 bases from the 5' end of the fragment.

The following oligonucleotides were used to prepare adapters:
oligonucleotide E 7788CGGCCGATGACCGTCGT-TGTCTGCA (SEQ ID NO: 11)
oligonucleotide F phosphate-GACAACGACGGTGTAGCCGG7887C (SEQ ID NO: 12)
oligonucleotide G 6655GCCGGCTACACCGTCGT-TGTCTGCA (SEQ ID NO: 13)

oligonucleotide H phosphate-GACAACGACGGTCATCGGCC6556G (SEQ ID NO: 14)

Where 5 represents dA-methylphosphonate 6 represents dG-methylphosphonate 7 represents dC-methylphosphonate 8 represents dT-methylphosphonate In example 3 adapters were ligated to two different samples of DNA, as follows:

Sample 1: Equimolar quantities of fragments SD1 and lambda 1700 were ligated to an adapter comprising oligonucleotides E and F that were complementary at the end which permits ligation but are mismatched at the other. The adapters also included a region of methylphosphonate linkages.

Sample 2: Equimolar quantities of fragments ES3 and lambda 1700 were ligated to an adapter comprising oligonucleotides G and H that were complementary at one end to permit ligation, but mismatched at the other. The adapters also included a region of methylphosphonate linkages.

Sequences E and F were fully complementary to H and G, respectively. When samples 1 and 2 were combined, denatured and allowed to reanneal, a mixture of different duplexes was anticipated comprising:

1. Matched homoduplexes of lambda or SD1, with adapters containing terminal mismatches, formed when the fragments from sample 1 reassociate.
2. A mixture of homoduplexes of lambda or ES3, with adapters containing terminal mismatches, formed when the fragments from sample 2 reassociate.
3. Heterohybrids of ES3 and SD1 fragments that contained a single base mismatch, but with perfectly matched adapters.
4. Homoduplexes of lambda with matched adapters formed when complementary strands, one each from samples 1 and 2 reanneal. The adapters in these molecules were also fully complementary.

The whole mixture was digested with T4 endonuclease VII, which will cleave one or both strands of DNA at a mismatch of one or more bases. In addition it will also cleave one strand of the terminally-mismatched adapters. A subsequent exonuclease III and S1 nuclease digestion will digest any duplexes cleaved by T4 endonuclease VII. Exonuclease III is a 3' to 5' exonuclease which, as shown in example 2, cannot digest DNA with methylphosphonate containing nucleotides. S1 is an endonuclease which specifically digests single stranded DNA. In this way, DNA which was not cleaved by T4 endonuclease VII would be protected from digestion by exonuclease III and S1 nuclease due to the presence of methylphosphonate nucleotides at the 3' ends of each duplex. Following the digestion steps, the remaining DNA could be amplified using an adapter specific primer.

In example 4 fragments SD1, ES1, ES3, ES4 and lambda 1700 were combined and the adapter formed by combining oligonucleotides E and H was ligated to them. In this way, the ends of the fragments were all protected by matched methylphosphonate containing adapters. The mixture was denatured and hybridised. A mixture of matched homoduplexes of lambda, SD1, ES1, ES3 or ES4 with perfectly matched adapters was anticipated when the fragments reassociate. In addition, mismatched duplexes with perfectly matched adapters were anticipated for the following:

| SD1 with ES1 | ES1 with ES3 |
| SD1 with ES3 | ES1 with ES4 |
| SD1 with ES4 | ES3 with ES4 |

The mixture was subjected to mismatch cleavage as described for example 3 above. Lambda 1700 fragments were expected to be resistant to digestion while any of the fragments forming mismatches were expected to be eliminated.

The post-digestion products were amplified, and subjected to a further round of denaturation, hybridisation, digestion and amplification. The amount of lambda 1700 fragments were anticipated to be increasingly enriched relative to the SD1/ES1/ES3/ES4 fragments, with each successive round of repetition of these steps.

EXAMPLE 3

Method

Southern Blot Hybridisation Analysis

The DNA samples removed at each stage of the procedure were analysed on an agarose gel stained with Vistra Green™ and viewed using a Fluorimager 595. The DNA from the gel was then transferred to Hybond-N+ nylon (Amersham Pharmacia Biotech) membrane according to the instructions provided by the manufacturer, and probed with a radio-labelled SD1 probe that hybridises to ES3. The membrane was then stripped and probed with a lambda 1700 probe of similar specific activity to the SD1 probe.

Ligation Reactions

The Lambda 1700 fragment and fragment SD1 were mixed in equimolar amounts and adapter comprising of oligonucleotides E and F was ligated to the fragments. The reaction was composed of 3.2 mM each oligonucleotide and 1×T4 ligase buffer. The concentration of the fragments in the reaction was 100 ng/µl. Similarly lambda 1700 and ES3 fragment were mixed in equimolar amounts. Adapters, comprising oligonucleotides G and H, were ligated to the mixture of fragments in a reaction with 4 mM each oligonucleotide, 1×T4 ligase buffer; the concentration of fragments in the reaction was 120 ng/µl. In parallel, adapters comprising oligonucleotides E and F or G and H were each independently ligated to human genomic DNA (67 ng/µl) that had been previously cut with PstI. These reactions comprised 6.7 mM each oligonucleotide, 1×T4 ligase buffer. The reactions were set up without ligase, incubated at 65° C. and allowed to cool slowly to 40° C. T4 DNA ligase was added to each reaction to a final concentration of 0.1 Units/µl and the reactions were incubated overnight at 37° C. Unligated adapters were removed using a microspin S-400 column. A 100% recovery of the fragments was assumed.

Denaturation and Hybridisation of Fragments

The hybridisation reactions were set up such that, assuming a 100% recovery as above, they contained 0.15 pmol each lambda 1700 bp and SD1 fragments and 500 ng of human genomic DNA ligated to adapter EF, together with 0.15 pmol each lambda 1700 bp and ES3 fragments and 500 ng human genomic DNA ligated to adapters GH.

The volume of each sample was made up with water to 45 µl and to each tube 1.2 µl 10% (v/v) Tween-20 (Pierce), 58 µl 2×hybridisation buffer (2.4M Sodium thiocyanate (Sigma), 0.2 M Phosphate pH 7.4, 4 mM EDTA pH 8.0) and 11.5 µl 90% (v/v) phenol (Sigma) was added. The samples were mixed and the solution appeared slightly turbid.

Samples were placed in a block preheated to 75° C. and incubated for 2 min. The tubes were then mixed to give a homogeneous solution. Samples were cycled as follows. 95° C. for 2 min followed by 70 cycles of 15 min at 22° C. and 2 min at 65° C. After cycling the reactions were transferred to a 1.5 ml tube containing 400 µl aqueous 0.1% Tween-20. 0.5 ml Phenol/chloroform/IAA (Sigma) was added, samples were vortexed and centrifuged for 5 min at 12000 rpm on a tabletop microcentrifuge. The aqueous phase was transferred to a fresh tube and washed with one volume of chloroform. Samples were then centrifuged at 12000 rpm for 5 min and the aqueous phase transferred to a fresh tube. 1 µl 1 mg/ml glycogen, 40 µl 3 M sodium acetate pH 5.2 and 0.7 volumes of isopropanol (Aldrich) were added and mixed. The samples were incubated at room temperature for 30 min before centrifugation at 12000 rpm for 10 min at room temperature. The pellets were then washed with 70% ice cold ethanol. After spinning for 5 min at 12000 rpm the ethanol was discarded and the pellet allowed to air dry. Each pellet was resuspended in 48 µl 1×Taq polymerase buffer. A 5 µl aliquot was removed for analysis.

T4 endonuclease VII Digestion

T4 endonuclease VII digestion was performed, in accordance with the manufacturers instructions, in a final volume of 50 µl with a 1000 Units of enzyme for at 37° C. for 15 min.

Following this digestion, an additional band of 800 bp was detected. This corresponded to the size of the larger specific cleavage product expected from the cleavage of ES3/SD1 heteroduplexes at the site of the mismatch.

Exonuclease III Digestion

For each reaction, Exonuclease III digestion was performed by adding 4 µl 250 mM NaCl, 1.6 µl buffer containing 0.1 M Tris-HCl pH 8.0 and 0.5 M MgCl$_2$, 1.2 µl water and 1.3 µl exonuclease III (250 units) and incubating at 37° C. for 10 minutes. Following digestion, a 15 µl aliquot was removed for analysis.

There was a considerable loss of DNA following the exonuclease III step, both ES3/SD1 fragments and lambda 1700 fragments appeared to have been digested to some extent. However, while the lambda 1700 band could still easily be seen on a blot of an agarose gel probed with SD1 and lambda probes, the SD1/ES3 band was not detected.

S1 nuclease Digestion

For the final digestion step, 1.2 µl S1 nuclease (16 units) was added to the Exonuclease III digested samples and the reaction was incubated at 37° C. for 15 minutes.

Following the S1 nuclease step it was difficult to detect any DNA on the agarose gel, however, on the blot of the gel, probed with lambda 1700 and SD1 probes, a clear, strong lambda 1700 band was present, while no SD1/ES3 fragment was detected. The expected outcome, i.e. the digestion of mismatched fragments concurrent with the conservation of identical fragments was therefore demonstrated. The final product could also be amplified by PCR using oligonucleotide G as a primer.

The above example has also been performed using a background of E. coli DNA with the same result: lambda 1700 fragment is retained while 1000 bp fragment is no longer detected at the end of the experiment.

The results for example 3 are summarised in tabulated form in Table 1.

TABLE 1

Summary of the results for example 3:

|  | Expected result | | Actual result | |
| --- | --- | --- | --- | --- |
|  | SD1/ES3 fragment | lambda 1700 fragment | SD1/ES3 fragment | lambda 1700 fragment |
| With human genomic DNA background | − | + | − | + |
| With E.coli genomic DNA background | − | + | − | + |

+ indicates that the fragment described could be detected on a Southern blot of the end products of example 3. The probe used for detection was specific for the fragments, either 1000 bp fragment (ES3 and SD1) or lambda 1700 fragment.

− indicates that the fragment of interest could not be detected on a Southern blot of the end products of example 3. The probe used for detection was specific for the fragments, either 1000 bp fragment (ES3 and SD1) or lambda 1700 fragment.

EXAMPLE 4

Method

Generation of Fragments

SD1, ES1, ES2, ES3 and ES4 PCR 1000 bp fragments and lambda 1700 bp fragment were ligated to adapters comprising oligonucleotides E and H essentially as described for example 3 using a 100-fold excess of the oligonucleotides. Approximately 0.5 ng of each of the ligated fragments were amplified by PCR using 20 pmoles oligonucleotide E as a primer in a 100 µl reaction containing 200 µM dNTPs and 5 units Taq polymerase in 1×Taq polymerase reaction buffer. After an initial denaturation step for 3 minutes at 94° C., twenty-five cycles of amplification were performed as follows; 94° C. for 30 seconds, 72° C. for 2 minutes. The reactions were purified on GFX columns and the products quantified using picogreen (Molecular probes) in accordance with manufacturers' instructions.

Denaturation and Hybridisation of Fragments

A pool of an equimolar amount of each of the five 1000 bp PCR products described above was prepared. A 25 ng aliquot of this pool was then mixed with an equimolar quantity of the lambda 1700 bp PCR product. This mixture of DNA fragments in a final volume of 30 µl of 1×Taq polymerase reaction buffer was denatured for 5 min at 95° C., cooled to 4° C. for 4 minutes before hybridisation at 65° C. for 30 minutes in an MJ Research thermal cycler. Following hybridisation an additional 20 µl of 1×Taq polymerase reaction buffer was added to each tube. A 2 µl aliquot of each reaction was removed for analysis.

T4 endonuclease VII Digestion

The remaining hybridisation reactions were supplemented with 1 µl of 2 µg/µl PstI digested E.coli DNA and digested, in accordance with the manufacturers' instructions, with 2000 Units of T4 Endonuclease VII in a final volume of 58 µl at 37° C. for 15 min. A 5.8 µl sample was removed from each reaction for analysis.

Exonuclease Digestion

An 8 µl aliquot of enzyme mix comprising 125 mM NaCl, 50 mM Tris pH 8, 15 mM MgCl, 12.5 units/µl T7 gene 6 exonuclease was added to the remaining amount of each T4 endonuclease VII digest. The reactions were then mixed and incubated for 10 min at 37° C. A 13.2 µl aliquot was removed from each reaction for analysis.

S1 nuclease Digestion

To the remaining amount of each reaction, 1.2 µl S1 nuclease (16 units) was added. The reactions were then incubated for 15 min at 37° C. and terminated by the addition of 5 µl 0.5M EDTA pH 8.0. A 15.1 µl aliquot was retained for later analysis.

Samples removed after each enzymatic step were run on a 1% agarose gel alongside serial dilutions of the ES2 1000 bp fragment and 1700 bp lambda fragment. The gel was post-stained with VistraGreen (1:10000) for 15 min and analysed on the FluorImager 595.

PCR Amplification for the Second Round of Hybridisation and Enzymatic Digestion

Duplicate tubes of products resulting from the first round of hybridisation and enzymatic digest described above, were combined and purified on GFX columns according to the manufacturers instructions. The samples were eluted in 100 µl of water and a 20 µl aliquot of this eluate was then used as template in a 100 µl PCR reaction containing 20 pmoles oligonucleotide G as primer, 200 µM dNTPs and 5 units Taq polymerase in 1×Taq polymerase reaction buffer. Following an initial denaturation step of 3 minutes at 94° C., twenty cycles of amplification were performed using the following conditions: 94° C., 30 seconds; 72° C. 2 minutes. The reactions were analysed by separating 15 µl of each reaction on a 1% agarose gel, stained and visualised as described above.

Result of the First Round

After the first round of hybridisation and enzymatic digestion of the reaction which initially contained a mixture of five different 1000 bp fragments and the 1700 bp lambda fragment, a 1700 bp product could be clearly seen corresponding to the lambda fragment. A faint 1000 bp band was also just detectable on the agarose gel corresponding to the ES1/ES2/ES3/ES4/SD1 fragments. In a control reaction, containing ES1 only, a clear band of 1000 bp was observed. These results demonstrated that following one round of hybridisation and enzymatic mismatch cleavage, the 1000 bp fragments that were capable of forming duplexes containing mismatches, were depleted relative to the lambda fragment which could only form perfectly matched duplexes.

Second Round of Hybridisation and Mismatch Digestion

The amplified material that survived the first round of hybridisation and enzymatic digestion was subjected to a second round essentially as described above. In the second round, however, 80 units T7 gene 6 exonuclease was added to each reaction instead of 100 units. Following S1 nuclease digestion, the products of the second round of the procedure were purified on GFX columns and eluted in 100 µl of water. A 40 µl aliquot was then used as a template for PCR amplification as described above.

Result of the Second Round

Following the second round of hybridisation and enzymatic digestion, the band corresponding to the 1700 bp lambda fragment was clearly visible following agarose gel electrophoresis. In contrast, a very faint band corresponding to the 1000 bp ES1/ES2/ES3/ES4/SD1 fragments was barely detectable. In the control reaction (starting population of ES1 1000 bp only) a clear 1000 bp band was detected following amplification.

Quantification of the agarose gel bands, corresponding to the end products of the first and second rounds of hybridisation and enzymatic digestion, demonstrated that the ratio of 1700 bp lambda fragment to total 1000 bp fragment showed additional enrichment at the end of the second round compared to the first.

Appendix 1

Lambda 1700 Sequence CTGCCCTGGCTGAGTGAGGC-CGACCGGCGGCTGCAGGTGCAGAGT-GATTTGCCGTGGTGGCTGGTC TGCCGGGGGAC-GATTCATAAGTTCCGCTGTGTGCCGCATCTCAC CGGGCGGCGCTTTGAGCACGGT GTGACGGACTGT-TACACACTGTTCCGGGATGCTTAT-CATCTGGCGGGGATTGAGATGCCGGACTTT CATCGTGAGGATGACTGGTGGCGTAACG-GCCAGAATCTCTATCTGGATAA
TCTGGAGGCGACGGGG CTGTATCAGGTGCCGT-TGTCAGCGGCACAGCCGGGCGATGTGCT-GCTGTGCTGTTTTGGTTCATCA GTGCCGAAT-CACGCCGCAATTTACTGCGGCGACGGCGAGCT GCTGCACCATATTC
CTGAACAACTG AGCAAACGAGAGAGGTACAC-CGACAAATGGCAGCGACGCACACACTC-CCTCTGGCGTCACCGGGCA TGGCGCGCATCTGC-CTTTACGGGGATTTACAACGATTTGGTCGCCGCA TCGACCTTCGTGTGAAAA CGGGGGCTGAAGC-CATCCGGGCACTGGCCACACAGCTCCCG-GCGTTTCGTCAGAAACTGAGCGACG GCTGGTAT-CAGGTACGGATTGCCGGGCGGGACGTCAGCAC GTCCGGGTTAA
CGGCGCAGTTACATG AGACTCTGCCTGATGGCGCT-GTAATTCATATTGTTCCCAGAGTCGC-CGGGGCCAAGTCAGGTGGCG TATTCCAGATTGTC-CTGGGGGCTGCCGCCATTGCCGGATCATTCTTTA CCGCCGGAGCCACCCTTG CAGCATGGGGGGCAGC-CATTGGGGCCGGTGGTATGACCGGCATC-CTGTTTTCTCTCGGTGCCAGTA TGGTGCTCGGTG-GTGTGGCGCAGATGCTGGCACCGAAAGCCAGAAC TCCCCGTATACAGACAACGG ATAACGGTAAGCA-GAACACCTATTTCTCCTCACTGGATAA-CATGGTTGCCCAGGGCAATGTTCTGC CTGTTCTG-TACGGGGAAATGCGCGTGGGGTCACGCGTGG TTTCTCAG
GAGATCAGCACGGCAGACG AAGGGGACGGTGGT-CAGGTTGTGGTGATTGGTCGCTGATG-CAAAATGTTTTATGTGAAACCGCCTG CGGG CGGTTTTGTCATTTATGGAGCGTGAG-GAATGGGTAAAGGAAGCAGTAAG
GGGCATACCCCGC GCGAAGCGAAGGACAACCT-GAAGTCCACGCAGTTGCTGAGTGTGATC-GATGCCATCAGCGAAGGGC CGATTGAAGGTCCG-GTGGATGGCTTAAAAAGCGTGCTGCTGA ACAGTACG
CCGGTGCTGGACACTG AGGGGAATACCAA-CATATCCGGTGTCACGGTGGTGTTC-CGGGCTGGTGAGCAGGAGCAGACTCCGC CGGAGGGATTTGAATCCTCCGGCTC-CGAGACGGTGCTGGGTACGGAAGTGAAAT ATGACACGCCGA TCACCCGCACCATTACGTCTG-CAAACATCGACCGTCTGCGCTTTACCT-TCGGTGTACAGGCACTGG TGGAAACCA CCTCAAAGGGTGACAGGAATCCGTCG-GAAGTCCGCCTGCTGGTT
CAGATACAACGTA ACGGTGGCTGGGTGACG-GAAAAAGACATCACCAT-TAAGGGCAAAACCACCTCGCAGTATCTGGCCT CGGTGGTGATGGGTAACCTGCCGC-CGCGCCCGTTTAATATCCGGATGCGCAGGATGA CGCCGGACA GCACCACAGACCAGCTGCAGAA-CAAAACGCTCTG (SEQ ID NO: 15)
pSD1 Sequence TCGCGCGTTTCGGTGATGACGGT-GAAAACCTCTGACACATGCAGCTCCCG-GAGACGGTCACAGCTT GTCTGTAAGCGGATGC-CGGGAGCAGACAAGCCCGTCAGGGCGCGTCAG CGGGTGTTGGCGGGTGTC GGGGCTGGCTTAACTAT-GCGGCATCAGAGCAGATTGTACT-GAGAGTGCACCATAAACGACATTACT ATATATATAATATAGGAAGCATTTAATA-GACAGCATCGTAATATATGTGTACTTTG CAGTTATGAC GCCAGATGGCAGTAGTGGAAGATAT-
TCTTTATTGAAAAATAGCTTGTCACCT-
TACGTACAATCTTG ATC
CGGAGCTTTTCTTTTTTTGCCGATTAA-
GAATTAATTCGGTCGAAAAAGAAAAG-
GAGAGGGCC AAGAGGGAGGGCATTGGTGACTAT-
TGAGCACGTGAGTATACGTGATTAAGCACACAA
AGGCAGCTT GGAGTATGTCTGTTATTAATTTCA-
CAGGTAGTTCTGGTCCATTGGT-
GAAAGTTTGCGGCTTGCAGA GCACAGAGGCCGCA
GAATGTGCTCTAGATTCCGATGCTGACTTGCTGGG
TATTATATGTGTGCCCA ATAGAAAGAGAACAAT-
TGACCCGGTTATTGCAAG-
GAAAATTTCAAGTCTTGTAAAAGCATATAAAA
ATAGTTCAGGCAC
TCCGAAATACTTGGTTGGCGTGTTTCG-
TAATCAACCTAAGGAGGATGTTTTGG CTCTGGT-
CAATGATTACGGCATTGATATCGTC-
CAACTGCATGGAGATGAGTCGTGGCAAGAATA
CCAAGAGTTCCTC
GGTTTGCCAGTTATTAAAAGACTCG-
TATTTCCAAAAGACTGCAACATACTACT CAGTG-
CAGCTTCACAGAAACCTCATTCGTTTAT-
TCCCTTGTTTGATTCAGAAGCAGGTGGGACAGG
TGAACTTTTGGATTGGAACT
CGATTTCTGACTGGGTTGGAAGGCAA-
GAGAGCCCCGAAAGCTTACA TTTTATGTTAGCTG-
GTGGACTGACGCCAGAAATGTTGGT-
GATGCGCTTAGATTAAATGGCGTTAT
TGGTGTTGATGTAAGCGGAG
GTGTGGAGACAAATGGTGTAAAA-
GACTCTAACAAAATAGCAAATTT CGTCAAAAAT-
GCTAAGAAATAGGTTATTACTGAGTAG-
TATTTATTTAAGTATTGTTTGTGCACTTG
CCTGCGGTGTGAAATACCGCACAGAT-
GCGTAAGGAGAAAATACCGCATCAG-
GAAATTGTAAACGTT AATATTTTGTTAAAAT-
TCGCGTTAAATTTTTGTTAAATCAGCTCATTTTTT
AACCAATAGGCCGAA ATCGGCAAAATCCCT-
TATAAATCAAAAGAATAGACCGAGAT-
AGGGTTGAGTGTTGTTCCAGTTTGG AACAA-
GAGTCCACTATTAAAGAACGTGGACTCCAACGT
CAAAGGGCGAAAAACCGTCTATCAGGGC GATGGC-
CCACTACGTGAACCATCACCCTAAT-
CAAGTTTTTTGGGGTCGAGGTGCC
GTAAAGCACTAAATCGGAACCCTAAAGGGAGC
CCCCGATTTAGAGCTTGACGGGGAAAGC-
CGGCGAACGTGGCGAGA AAGGAAGGGAA-
GAAAGCGAAAG-
GAGCGGGCGCTAGGGCGCTGGCAAGTGTAGCG
GTCACGCTGCGC GTAACCACCACACCCGC-
CGCGCTTAATGCGCCGCTA-
CAGGGCGCGTCGCGCCATTCGCCATTCAGG
CTGCGCAACTGTTGGGAAGGGCGATCG-
GTGCGGGCCTCTTCGCTATTACGCCAGCT
GGCGAAGGGG GGATGTGCTGCAAGGCGATTAAGT-
TGGGTAACGCCAGGGTTTTCCCAGTCAC-
GACGTTGTAAAACG ACGGCCAGTGAATTG-
TAATACGACTCACTATAGGGCGAATTGGAGCTC
GAGCAATAAAGATTCTAC AATACTAGCTTTTATGGT-
TATGAAGAGGAAAAATTGGCAGTAAC-
CTGGCCCCACAAACCTTCAAAT GAACGAAT-
CAAATTAACAACCATAGGATGATAATGCGATTA
GTTTTTTAGCCTTA
TTCTGGGGTA ATTAATCAGCGAAGCGAT-
GATTTTTGATCTATTAACA-
GATATATAAATGCAAAAACTGCATAACCA CTT-
TAACTAATACTTTCAACATTTTCGGTTTGTATTAC
TTCTTATTCAAATGTAATAAAAGTATCA ACATCTA-
GAATTCCATGGAA
TCGATGCGGCCGCAATTCATCGATTA-
GACTAGTCTAGATATCATGT AATTAGTTATGT-
CACGCTTACATTCACGCCCTCCCCCA-
CATCCGCTCTAACCGAAAAGGAAGGAG
TTAGACAACCTGAAGTCTAGGTC-
CCTATTTATTTTTTATAGTTATGTTAG-
TATTAAGAACGTTAT
TTATATTTCAAATTTTTCTTTTTTTCT-
GTACAGACGCGTGTACGCATGTAACAT-
TATACTGAAAA CCTTGCTTGAGAAGGTTTTGG-
GACGCTCGAAGGCTTTAATTTGCGGTACCCAG
CTTTTGTTCCCTT TAGTGAGGGTTAATTCCGAGCT-
TGGCGTAATCATGGTCATAGCTGTTTC-
CTGTGTGAAATTGTTAT CCGCTCACAATTCCACA-
CAA
CATAGGAGCCGGAAGCATAAAGTG-
TAAAGCCTGGGGTGCCTAATGA GTGAGGTAACT-
CACATTAATTGCGTTGCGCTCACTGC-
CCGCTTTCCAGTCGGGAAACCTGTCGTGC
CAGCTGCATTAATGAATCGGC-
CAACGCGCGGGGAGAGGCGGTTTGCG-
TATTGGGCGCTCTTCCGCT TCCTCGCTCACT-
GACTCGCTGCGCTCGGTCGTTCGGCTGCGGCGA
GCGGTATCAGCTCACTCAAAG GCGGTAATACGGT-
TATCCACAGAATCAGGGGATAACGCAG-
GAAAGAACATGTGAGCAAAAGGCCAG CAAAAG-
GCCAGGAACCGTAAAAAGGCCGCGTTGCTGGC
GTTTTTCCATAG
GCTCGGCCCCCTGAC GAGCATCACAAAAATC-
GACGCTCAAGTCAGAGGTGGCGAAAC-
CCGACAGGACTATAAAGATACCAG GCGTTC-
CCCCCTGGAAGCTCCCTCGTGCGCTCTCCTGTT
CCGACCCTGCCGCT
TACCGGATACCTG TCCGCCTTTCTCCCTTCGG-
GAAGCGTGGCGCTTTCTCAATGCT-
CACGCTGTAGGTATCTCAGTTCG GTGTAGGTCGT-
TCGCTCCAAGCTGGGCTGTGTGCACGAACCCC
CCGTTC
AGCCCGACCGCTGCGCC TTATCCGGTAAC-
TATCGTCTTGAGTCCAACCCGGTAAGA-
CACGACTTATCGCCACTGGCAGCAGCC ACTGG-
TAACAGGATTAGCAGAGCGAGGTATGTAGGCG
GTGCTACAGAGTTCT
TGAAGTGGTGGCCT AACTACGGCTACACTAGAAG-
GACAGTATTTGGTATCTGCGCTCTGCT-
GAAGCCAGTTACCTTCGGA AAAAGAGTTGG-
TAGCTCTTGATCCGGCAAACAAACCACCGCTG
GTAGCGGT
GGTTTTTTTGTTTGC AAGCAGCAGATTACGCGCA-
GAAAAAAAGGATCTCAAGAAGATC-
CTTTGATCTTTTCTACGGGGTCT GACGCTCAGTG-
GAACGAAAACTCACGTTAAGGGATTTTGGTCAT
GAGATTATCAA
AAAGGATCTTC ACCTAGATCCTTTTAAAT-
TAAAAATGAAGTTTTAAAT-
CAATCTAAAGTATATATGAGTAAACTTGG TCTGA-
CAGTTACCAATGCTTAATCAGTGAGGCACCTATC
TCAGCGATCTG
TCTATTTCGTTCATCC ATAGTTGCCTGACTGC-
CCGTCGTGTAGATAACTACGATACGG-
GAGGGCTTACCATCTGGCCCCAGT GCTGCAAT-
GATACCGCGAGACCCACGCTCACCGGCTCCAG
ATTTATCAG
CAATAAACCAGCCAGCC GGAAGGGCCGAGCGCA- GAAGTGGTCCTGCAACTTTATCCGCCTC-
CATCCAGTCTATTAATTGTTGC CGGGAAGCTAGAG-
TAAGTAGTTCGCCAGTTAATAGTTTGCGCAACG
TTGTTGCCATTG
CTACAGGC ATCGTGGTGTCACGCTCGTCGTTTGG-
TATGGCTTCATTCAGCTCCGGTTC-
CCAACGATCAAGGCGA GTTACATGATCCCCCATGT-
TGTGAAAAAAAGCGGTTAGCTCCTTCGGTCCTC
CGATCGTTGTCAGA AGTAAGTTGGCCGCAGTGT-
TATCACTCATGGTTATGGCAGCACTG-
CATAATTCTCTTACTGTCATG CCATCCGTAAGAT-
GCTTTTCTGTGACTGGTGAGTACTCAACCAAGT
CATTCTGA
GAATAGTGTATG CGGCGACCGAGTTGCTCTTGC-
CCGGCGTCAATACGGGATAATACCGCGC-
CACATAGCAGAACTTTA AAAGTGCTCATCATTG-
GAAAACGTTCTTCGGGGCGAAAACTCTCAAGG
ATCTTACCGCTGTTGAGA TCCAGTTCGATGTAAC-
CCACTCGTGCACCCAACTGATCTTCAG-
CATCTTTTACTTTCACCAGCGTT TCTGGGTGAG-
CAAAAACAGGAAGGCAAAATGCCGCAAAAAAG
GGAATA
AGGGCGACACGGAAATGT TGAATACTCATACTCT-
TCCTTTTTCAATATTATTGAAGCATT-
TATCAGGGTTATTGTCTCATGAGC GGATA-
CATATTTGAATGTATTTAGAAAAATAAACAAATA
GGGGTTCCGCGCACATTTCCCCGAAAA GTGCCAC-
CTGGGTCCTTTTCATCACGTGC-
TATAAAAATAATTATAATTTAAATTTTTTAATATAAA
TATATAAATTAAAAATAGAAAG-
TAAAAAAAGAAATTAAAGAAAAAATAG
TTTTTGTTTTCCGAAGA TGTAAAAGACTCTAGGGG-
GATCGCCAACAAATACTACCTTTTATCT-
TGCTCTTCCTGCTCTCAGGT ATTAATGCCGAAT-
TGTTTCATCTTGTCTGTGTAGAAGACCACACAC
GAAAATCCT
GTGATTTTACA TTTTACTTATCGTTAATCGAATG-
TATATCTATTTAATCTGCTTTTCT-
TGTCTAATAAATATATATG TAAAGTACGCTTTTTGT-
TGAAATTTTTTAAACCTTTGTTTATTTTTTTTT
CTTCATTCCGTAACTC TTCTACCTTCTTTATT-
TACTTTCTAAAATCCAAATACAAAACAT-
AAAAATAAATAAACACAGAGTA AATTCCCAAAT-
TATTCCATCATTAAAAGATACGAGGCGCGTGTAA
GTTACAGGCAAGCGATCCGTC CTAAGAAACCAT-
TATTATCATGACATTAACCTATAAAAAT-
AGGCGTATCACGAGGCCCTTTCGTC (SEQ ID NO: 16)

The sequences of the other plasmids vary only at the series of six bases 'GATATC' shown in bold and larger font size than the rest of the sequence, on the sequence above. These variations are as follows:

| | |
|---|---|
| SD1 | GATATC |
| ES1 | AATATC |
| ES3 | CATATC |
| ES4 | -ATATC |

The sequence of the primers used to amplify 1000 bp fragments with ends including PstI sites from all of the plasmids were as follows. Their positions in the plasmid are underlined:

Forward: GAACTGCAGCTAGATTCCGATGCTGACT-
TGCT (SEQ ID NO: 17)

Reverse: TCCCTGCAGGGTTCCGATTTAGTGCTT-
TAC (SEQ ID NO: 18)

Following PCR, the products were digested with PstI.

What is claimed is:

1. A method of performing genomic analysis by:
   i) providing genomic DNA, pooled from a plurality of individuals that share a phenotype;
   ii) digesting the genomic DNA to provide genomic fragments whose average length is greater than the average spacing between natural polymorphisms;
   iii) ligating an adapter to each end of each genomic fragment produced in step ii), said adapter being, when in double-stranded mismatch-free form, resistant to nuclease digestion;
   iv) denaturing and re-annealing the mixture of adapter-terminated genomic fragments produced in step iii);
   v) removing from the mixture produced in step iv) hybrids containing mismatches and if required amplifying mismatch-free hybrids;
   vi) and repeating steps iv) and v) to recover one or a few mismatch-free hybrids associated with the phenotype.

2. The method of claim 1, wherein the one or a few mismatch-free hybrids recovered in step vi) are analysed by hybridisation to reference sequences of nucleic acid.

3. The method of claim 1, wherein a mismatch-free hybrid resulting from step vi) is sequenced.

4. A method of performing genomic analysis by:
   i) providing first nucleic acid, pooled from a plurality of individuals that share a phenotype;
   ii) digesting the said first nucleic acid to provide fragments whose average length is about equal to or less than the average spacing between natural polymorphisms;
   iii) ligating an adapter to each end of each fragment produced in step ii) to form adapter-terminated nucleic acid fragments which are, when in double-stranded mismatch-free form, resistant to nuclease digestion;
   iv) denaturing and re-annealing the mixture of adapter-terminated nucleic acid fragments produced in step iii);
   v) removing from the mixture produced in step iv) hybrids containing mismatches and if required amplifying mismatch-free hybrids;
   vi) repeating steps iv) and v) to recover a first mixture of mismatch-free hybrids;
   vii) providing second nucleic acid pooled from a plurality of individuals that do not share the same phenotype;
   viii) subjecting the nucleic acid of vii) to the said steps ii) to vi) to recover a second mixture of mismatch-free hybrids;
   ix) combining under hybridisation conditions single strands of the said first mixture of mismatch-free hybrids and the said second mixture of mismatch-free hybrids;
   x) and recovering nucleic acid fragments that do not form mismatch-free hybrids and are associated with the phenotype.

5. The method of claim 4, wherein the nucleic acid fragments recovered in step x) are analysed by hybridisation to reference sequences of nucleic acid.

6. The method of claim 4, wherein the nucleic acid fragments recovered in step x) are sequenced.

7. The method of claim 4, wherein the nucleic acid is genomic DNA.

8. The method of claim 4, wherein the nucleic acid represents a subset of the genome that is transcribed in a tissue or tissues of interest.

9. The method of claim 4, wherein step x) is performed by physical separation of mismatched fragments following binding to at least one mismatch specific protein.

10. The method of claim 1, wherein the adapter comprises phosphodiester bonds, selected from phosphorothioate and methylphosphonate, that are nuclease resistant.

11. The method of claim 1, wherein in step v) hybrids containing mismatches are removed by means of a mismatch recognition protein and an exonuclease/endonuclease combination.

* * * * *